(12) United States Patent
Matsuura et al.

(10) Patent No.: US 11,975,080 B2
(45) Date of Patent: May 7, 2024

(54) ANTI-MESOTHELIN POLYPEPTIDE, AND TUMOR IMAGING AGENTS AND COMPLEXES THEREOF

(71) Applicant: NATIONAL UNIVERSITY CORPORATION OKAYAMA UNIVERSITY, Okayama (JP)

(72) Inventors: Eiji Matsuura, Okayama (JP); Kazuko Kobayashi, Okayama (JP); Fumiaki Takenaka, Okayama (JP)

(73) Assignee: NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 682 days.

(21) Appl. No.: 16/759,960

(22) PCT Filed: Mar. 27, 2018

(86) PCT No.: PCT/JP2018/012391
§ 371 (c)(1),
(2) Date: Apr. 28, 2020

(87) PCT Pub. No.: WO2019/087425
PCT Pub. Date: May 9, 2019

(65) Prior Publication Data
US 2020/0324001 A1    Oct. 15, 2020

(30) Foreign Application Priority Data
Oct. 31, 2017 (JP) ................................ 2017-210508

(51) Int. Cl.
| | | |
|---|---|---|
| *C07K 16/28* | (2006.01) | |
| *A61K 47/66* | (2017.01) | |
| *A61K 51/10* | (2006.01) | |
| *C07K 14/47* | (2006.01) | |
| *C07K 19/00* | (2006.01) | |

(52) U.S. Cl.
CPC .......... *A61K 51/1054* (2013.01); *A61K 47/66* (2017.08); *C07K 14/4748* (2013.01)

(58) Field of Classification Search
None
See application file for complete search history.

(56) References Cited

U.S. PATENT DOCUMENTS

| 7,081,518 B1 | 7/2006 | Pastan et al. |
| 2016/0311917 A1 | 10/2016 | Beatty et al. |
| 2018/0244796 A1 | 8/2018 | Wang et al. |

FOREIGN PATENT DOCUMENTS

| AU | 2012254877 A1 | 12/2012 |
| CN | 101012280 A | 8/2007 |
| CN | 106467573 A | 3/2017 |
| JP | 2003-502030 A | 1/2003 |
| JP | 2011-504372 A | 2/2011 |
| JP | 2014-221064 A | 11/2014 |
| WO | WO 1999/028471 A2 | 6/1999 |
| WO | WO 2000/073346 A1 | 12/2000 |
| WO | WO 2009/068204 A1 | 6/2009 |
| WO | WO 2010/111282 A1 | 9/2010 |
| WO | WO 2011/074621 A1 | 6/2011 |

OTHER PUBLICATIONS

Hassan et al., "Mesothelin: A New Target for Immunotherapy," Clin. Cancer Res., 10(12 Pt. 1): 3937-3942 (2004).
Hassan et al., "Mesothelin targeted cancer immunotherapy," Eur. J. Cancer, 44(1): 46-53 (2008).
Hassan et al., "Inhibition of mesothelin-CA-125 interaction in patients with mesothelioma by the anti-mesothelin monoclonal antibody MORAb-009: Implications for cancer therapy," Lung Cancer, 68(3): 455-459 (2010).
Ho et al., "A novel high-affinity human monoclonal antibody to mesothelin," Int. J. Cancer, 128(9): 2020-2030 (2011).
Kobayashi et al., "A Novel PET Imaging Using $^{64}$Cu-Labeled Monoclonal Antibody against Mesothelin Commonly Expressed on Cancer Cells," J. Immunol. Res., 2015: 268172 (2015).
Matsuura, "Development of targeted therapy of cancer cells with diagnostic imaging through the application of immunoliposomes," Grants-in-Aid for Scientific Research (KAKEN), Project/Area No. 23659299 (Mar. 31, 2013).
Terwisscha Van Scheltinga, "Preclinical Efficacy of an Antibody-Drug Conjugate Targeting Mesothelin Correlates with Quantitative $^{89}$Zr-ImmunoPET," Mol. Cancer Ther., 16(1): 134-142 (2017).
Zhang et al., "New High Affinity Monoclonal Antibodies Recognize Non-Overlapping Epitopes on Mesothelin for Monitoring and Treating Mesothelioma," Sci. Rep., 5: 09928 (2015).
Japanese Patent Office, International Search Report in International Patent Application No. PCT/JP2018/012391 (dated Jun. 19, 2018) English translation.
Chen et al., "Preparation and Characterization of the Monoclonal Antibody Against Human Soluble Mesothelin-related Proteins," Chin. J. Cell. Mol. Immunol., 23(3): 246-248 (2007).
China National Intellectual Property Administration, Office Action in Chinese Patent Application No. 201880068618.8 (dated Oct. 26, 2022).

*Primary Examiner* — Christine J Saoud
*Assistant Examiner* — Jon M Lockard
(74) *Attorney, Agent, or Firm* — Leydig, Voit & Mayer, Ltd.

(57) ABSTRACT

This invention provides a DNA comprising any of the following (a) to (c): (a) a DNA comprising any of the base sequences of positions 16 to 831 of SEQ ID NO: 1, positions 16 to 822 of SEQ ID NO: 3, positions 16 to 825 of SEQ ID NO: 5, positions 16 to 819 of SEQ ID NO: 7, positions 16 to 834 of SEQ ID NO: 9, and positions 16 to 828 of SEQ ID NO: 11; (b) a DNA encoding a polypeptide comprising any of the amino acid sequences of positions 1 to 272 of SEQ ID NO: 2, positions 1 to 269 of SEQ ID NO: 4, positions 1 to 270 of SEQ ID NO: 6, positions 1 to 268 of SEQ ID NO: 8, positions 1 to 273 of SEQ ID NO: 10, and positions 1 to 271 of SEQ ID NO: 12; and (c) a complementary strand of the DNA (a) or (b).

4 Claims, 9 Drawing Sheets

Specification includes a Sequence Listing.

Fig. 9

MSLNH1a050LHscFv

```
             HindIII Kozak        VL leader (signal peptide)
                            M A S F P L L L T L L T H C A G S W A  S Y E
         AAGCTTGCCGCCACCATGGCCAGCTTCCCTCTGCTGCTGACGCTCCTCACTCACTGTGCAGGATCCTGGGCGTCGTATGA L T Q P P S V S V S P G Q T A R I T C  CDRL1
                                                  S G N A L P K
 81      GCTGAGTCAGCCACCCTCGGTGTCAGTGTCCCCAGGACAGACGGCCAGGATCACCTGC TCTGGAAATGCATTGCCAAAGC  160
                                                                         CDRL2
            Q Y A Y  W Y Q Q K P G Q A P V L M I Y  K D S E R P S  G
161      AATATGCTTAT GGTACCAGCAGAAGCCAGGCCAGGCCCTGTGTTGATGATATAT AAAGACAGTGAGAGGCCCTCA GGG  240

I P E R F S G S S S G T T V T L T I S G V Q A E D E A
241      ATCCCTGAGCGATTCTCTGGCTCCAGCTCAGGGACAACAGTCACGTTGACCATCAGTGGAGTCCAGGCAGAAGACGAGGC  320
                                CDRL3
            D Y Y C  Q S A D S S H T Y K V  F G G G T K L T V L G
321      TGACTATTACTGT CAATCAGCAGACAGCAGTCATACTTATAAGGTG TTCGGCGGAGGGACCAAGCTGACCGTCCTAGGCG  400
                  Linker
            G G G S G G G G S G G G G S G G G G S E V Q L V Q S G
401      GTGGCGGATCAGGTGGCGGTGGAAGTGGCGGTGGTGGGTCTGGAGGTGGGGGCAGTGAGGTGCAGCTGGTGCAGTCTGGG  480
                                                                       CDRH1
            G G L V Q P D R S L R L S C A A S G F T F D  D Y A M H
481      GGAGGCTTGGTACAGCCTGACAGGTCCCTGAGACTCTCCTGTGCAGCCTCTGGATTCACCTTTGAT GATTATGCCATGCA  560
                                                  CDRH2
            W V R Q A P G K G L E W V S  G I S W N S G S I G Y A
561      CTGGGTCCGGCAAGCTCCAGGGAAGGGCCTGGAGTGGGTCTCA GGTATTAGTTGGAATAGTGGTAGCATAGGCTATGCGG  640

D S V K G  R F T I S R D N A K N S L Y L Q M N S L R A
641      ACTCTGTGAAGGGC CGATTCACCATCTCCAGAGACAACGCCAAGAACTCCCTGTATCTGCAAATGAACAGTCTGAGAGCT  720
                             CDRH3
            E D T A L Y Y C A K  D L G S Y Y G S G S G M D V  W G Q
721      GAGGACACGGCCTTGTATTACTGTGCAAAA GATCTGGGGTCCTACTATGGTTCGGGGAGTGGTATGGACGTC TGGGGCCA  800
                             His tag
            G T T V T V S S  H H H H H H       EcoRI
801      AGGGACCACGGTCACCGTCTCGAGC CACCATCATCATCACCACTAGTGA GAATTC  861
```

FIG. 11
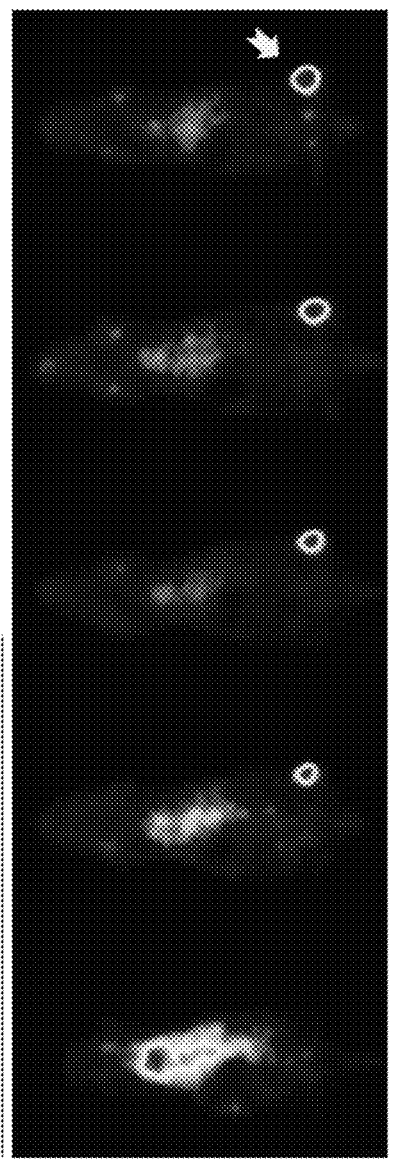
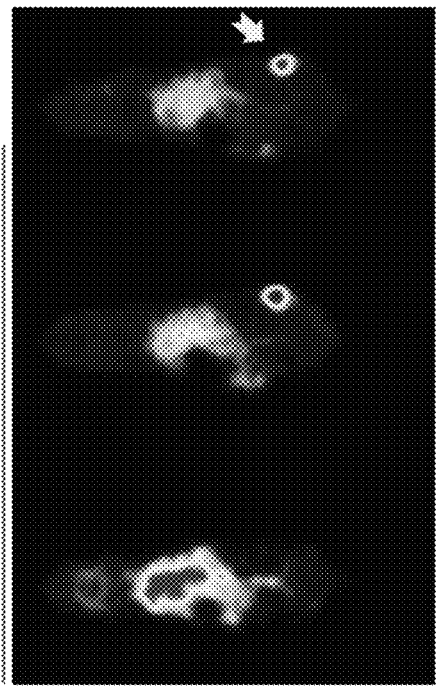

SEQUENCE LISTING

```
<160> NUMBER OF SEQ ID NOS: 12

<210> SEQ ID NO 1
<211> LENGTH: 861
<212> TYPE: DNA
<213> ORGANISM: Artificial Sequence
<220> FEATURE:
<223> OTHER INFORMATION: Synthetic Sequence - MSLNH1a050LHscFv
<220> FEATURE:
<221> NAME/KEY: CDS
<222> LOCATION: (16)..(855)

<400> SEQUENCE: 1
aagcttgccg ccacc atg gcc agc ttc cct ctc ctc ctc acc ctc ctc act    51
                Met Ala Ser Phe Pro Leu Leu Leu Thr Leu Leu Thr
```

|  | 1 |  |  |  | 5 |  |  |  |  | 10 |  |  |  |  |
|---|---|---|---|---|---|---|---|---|---|---|---|---|---|---|
| cac | tgt | gca | gga | tcc | tgg | gcc | tcc | tat | gag | ctg | act | cag | cca | ccc tcg | 99 |
| His | Cys | Ala | Gly | Ser | Trp | Ala | Ser | Tyr | Glu | Leu | Thr | Gln | Pro | Pro Ser |  |
|  |  | 15 |  |  |  | 20 |  |  |  |  | 25 |  |  |  |

| gtg | tca | gtg | tcc | cca | gga | cag | acg | gcc | agg | atc | acc | tgc | tct | gga aat | 147 |
| Val | Ser | Val | Ser | Pro | Gly | Gln | Thr | Ala | Arg | Ile | Thr | Cys | Ser | Gly Asn |  |
|  | 30 |  |  |  |  | 35 |  |  |  |  | 40 |  |  |  |

| gca | ttg | cca | aag | caa | tat | gct | tat | tgg | tac | cag | cag | aag | cca | ggc cag | 195 |
| Ala | Leu | Pro | Lys | Gln | Tyr | Ala | Tyr | Trp | Tyr | Gln | Gln | Lys | Pro | Gly Gln |  |
| 45 |  |  |  |  | 50 |  |  |  |  | 55 |  |  |  | 60 |

| gcc | cct | gtg | ttg | atg | ata | tat | aaa | gac | agt | gag | agg | ccc | tca | ggg atc | 243 |
| Ala | Pro | Val | Leu | Met | Ile | Tyr | Lys | Asp | Ser | Glu | Arg | Pro | Ser | Gly Ile |  |
|  |  |  |  | 65 |  |  |  |  | 70 |  |  |  |  | 75 |

| cct | gag | cga | ttc | tct | ggc | tcc | agc | tca | ggg | aca | aca | gtc | acg | ttg acc | 291 |
| Pro | Glu | Arg | Phe | Ser | Gly | Ser | Ser | Ser | Gly | Thr | Thr | Val | Thr | Leu Thr |  |
|  |  |  | 80 |  |  |  |  | 85 |  |  |  |  | 90 |  |

| atc | agt | gga | gtc | cag | gca | gaa | gac | gag | gct | gac | tat | tac | tgt | caa tca | 339 |
| Ile | Ser | Gly | Val | Gln | Ala | Glu | Asp | Glu | Ala | Asp | Tyr | Tyr | Cys | Gln Ser |  |
|  |  | 95 |  |  |  |  | 100 |  |  |  |  | 105 |  |  |

| gca | gac | agc | agt | cat | act | tat | aag | gtg | ttc | ggc | gga | ggg | acc | aag ctg | 387 |
| Ala | Asp | Ser | Ser | His | Thr | Tyr | Lys | Val | Phe | Gly | Gly | Gly | Thr | Lys Leu |  |
|  | 110 |  |  |  |  | 115 |  |  |  |  | 120 |  |  |  |

| acc | gtc | cta | ggc | ggt | ggc | gga | tca | ggt | ggc | ggt | gga | agt | ggc | ggt ggt | 435 |
| Thr | Val | Leu | Gly | Gly | Gly | Gly | Ser | Gly | Gly | Gly | Gly | Ser | Gly | Gly Gly |  |
| 125 |  |  |  |  | 130 |  |  |  |  | 135 |  |  |  | 140 |

| ggg | tct | gga | ggt | ggg | ggc | agt | gag | gtg | cag | ctg | gtg | cag | tct | ggg gga | 483 |
| Gly | Ser | Gly | Gly | Gly | Gly | Ser | Glu | Val | Gln | Leu | Val | Gln | Ser | Gly Gly |  |
|  |  |  |  | 145 |  |  |  |  | 150 |  |  |  |  | 155 |

| ggc | ttg | gta | cag | cct | gac | agg | tcc | ctg | aga | ctc | tcc | tgt | gca | gcc tct | 531 |
| Gly | Leu | Val | Gln | Pro | Asp | Arg | Ser | Leu | Arg | Leu | Ser | Cys | Ala | Ala Ser |  |
|  |  |  | 160 |  |  |  |  | 165 |  |  |  |  | 170 |  |

| gga | ttc | acc | ttt | gat | gat | tat | gcc | atg | cac | tgg | gtc | cgg | caa | gct cca | 579 |
| Gly | Phe | Thr | Phe | Asp | Asp | Tyr | Ala | Met | His | Trp | Val | Arg | Gln | Ala Pro |  |
|  |  | 175 |  |  |  |  | 180 |  |  |  |  | 185 |  |  |

| ggg | aag | ggc | ctg | gag | tgg | gtc | tca | ggt | att | agt | tgg | aat | agt | ggt agc | 627 |
| Gly | Lys | Gly | Leu | Glu | Trp | Val | Ser | Gly | Ile | Ser | Trp | Asn | Ser | Gly Ser |  |
|  | 190 |  |  |  |  | 195 |  |  |  |  | 200 |  |  |  |

| ata | ggc | tat | gcg | gac | tct | gtg | aag | ggc | cga | ttc | acc | atc | tcc | aga gac | 675 |
| Ile | Gly | Tyr | Ala | Asp | Ser | Val | Lys | Gly | Arg | Phe | Thr | Ile | Ser | Arg Asp |  |
| 205 |  |  |  |  | 210 |  |  |  |  | 215 |  |  |  | 220 |

| aac | gcc | aag | aac | tcc | ctg | tat | ctg | caa | atg | aac | agt | ctg | aga | gct gag | 723 |
| Asn | Ala | Lys | Asn | Ser | Leu | Tyr | Leu | Gln | Met | Asn | Ser | Leu | Arg | Ala Glu |  |
|  |  |  |  | 225 |  |  |  |  | 230 |  |  |  |  | 235 |

| gac | acg | gcc | ttg | tat | tac | tgt | gca | aaa | gat | ctg | ggg | tcc | tac | tat ggt | 771 |
| Asp | Thr | Ala | Leu | Tyr | Tyr | Cys | Ala | Lys | Asp | Leu | Gly | Ser | Tyr | Tyr Gly |  |
|  |  |  | 240 |  |  |  |  | 245 |  |  |  |  | 250 |  |

| tcg | ggg | agt | ggt | atg | gac | gtc | tgg | ggc | caa | ggg | acc | acg | gtc | acc gtc | 819 |
| Ser | Gly | Ser | Gly | Met | Asp | Val | Trp | Gly | Gln | Gly | Thr | Thr | Val | Thr Val |  |
|  |  | 255 |  |  |  |  | 260 |  |  |  |  | 265 |  |  |

| tcg | agc | ggg | ggt | cat | cat | cac | cac | cac | cac | tag | tga | gaattc |  |  | 861 |
| Ser | Ser | Gly | Gly | His | His | His | His | His | His |  |  |  |  |  |  |
|  | 270 |  |  |  |  | 275 |  |  |  |  |  |  |  |  |

<210> SEQ ID NO 2
<211> LENGTH: 278
<212> TYPE: PRT
<213> ORGANISM: Artificial Sequence
<220> FEATURE:
<223> OTHER INFORMATION: Synthetic Sequence - MSLNH1a050LHscFv

<400> SEQUENCE: 2

```
Met Ala Ser Phe Pro Leu Leu Leu Thr Leu Leu Thr His Cys Ala Gly
1               5                   10                  15

Ser Trp Ala Ser Tyr Glu Leu Thr Gln Pro Ser Val Ser Val Ser
            20                  25                  30

Pro Gly Gln Thr Ala Arg Ile Thr Cys Ser Gly Asn Ala Leu Pro Lys
            35                  40                  45

Gln Tyr Ala Tyr Trp Tyr Gln Gln Lys Pro Gly Gln Ala Pro Val Leu
        50                  55                  60

Met Ile Tyr Lys Asp Ser Glu Arg Pro Ser Gly Ile Pro Glu Arg Phe
65                  70                  75                  80

Ser Gly Ser Ser Ser Gly Thr Thr Val Thr Leu Thr Ile Ser Gly Val
                85                  90                  95

Gln Ala Glu Asp Glu Ala Asp Tyr Tyr Cys Gln Ser Ala Asp Ser Ser
            100                 105                 110

His Thr Tyr Lys Val Phe Gly Gly Gly Thr Lys Leu Thr Val Leu Gly
            115                 120                 125

Gly Gly Gly Ser Gly Gly Gly Gly Ser Gly Gly Gly Gly Ser Gly Gly
        130                 135                 140

Gly Gly Ser Glu Val Gln Leu Val Gln Ser Gly Gly Gly Leu Val Gln
145                 150                 155                 160

Pro Asp Arg Ser Leu Arg Leu Ser Cys Ala Ala Ser Gly Phe Thr Phe
            165                 170                 175

Asp Asp Tyr Ala Met His Trp Val Arg Gln Ala Pro Gly Lys Gly Leu
        180                 185                 190

Glu Trp Val Ser Gly Ile Ser Trp Asn Ser Gly Ser Ile Gly Tyr Ala
            195                 200                 205

Asp Ser Val Lys Gly Arg Phe Thr Ile Ser Arg Asp Asn Ala Lys Asn
        210                 215                 220

Ser Leu Tyr Leu Gln Met Asn Ser Leu Arg Ala Glu Asp Thr Ala Leu
225                 230                 235                 240

Tyr Tyr Cys Ala Lys Asp Leu Gly Ser Tyr Tyr Gly Ser Gly Ser Gly
            245                 250                 255

Met Asp Val Trp Gly Gln Gly Thr Thr Val Thr Val Ser Ser Gly Gly
            260                 265                 270

His His His His His His
        275
```

<210> SEQ ID NO 3
<211> LENGTH: 852
<212> TYPE: DNA
<213> ORGANISM: Artificial Sequence
<220> FEATURE:
<223> OTHER INFORMATION: Synthetic Sequence - MSLNH2a021LHscFv
<220> FEATURE:
<221> NAME/KEY: CDS
<222> LOCATION: (16)..(846)

<400> SEQUENCE: 3

```
aagcttgccg ccacc atg gcc agc ttc cct ctc ctc ctc acc ctc ctc act      51
                Met Ala Ser Phe Pro Leu Leu Leu Thr Leu Leu Thr
                1               5                   10 cac tgt gca gga tcc tgg gcc tct tct gag ctg act cag gac cct gct      99
His Cys Ala Gly Ser Trp Ala Ser Ser Glu Leu Thr Gln Asp Pro Ala
        15                  20                  25 gtg tct gtg gcc ttg gga cag aca gtc agg atc aca tgc caa gga gac     147
Val Ser Val Ala Leu Gly Gln Thr Val Arg Ile Thr Cys Gln Gly Asp
    30                  35                  40
```

```
agc ctc aga agc tat tat gca agc tgg tac cag cag aag cca gga cag         195
Ser Leu Arg Ser Tyr Tyr Ala Ser Trp Tyr Gln Gln Lys Pro Gly Gln
 45              50                  55                  60 gcc cct gta ctt gtc atc tat ggt aaa aac aac cgg ccc tca ggg atc         243
Ala Pro Val Leu Val Ile Tyr Gly Lys Asn Asn Arg Pro Ser Gly Ile
             65                  70                  75 cca gac cga ttc tct ggc tcc agc tca gga aac aca gct tcc ttg acc         291
Pro Asp Arg Phe Ser Gly Ser Ser Ser Gly Asn Thr Ala Ser Leu Thr
                 80                  85                  90 atc act ggg gct cag gcg gaa gat gag gct gac tat tac tgt cag gcg         339
Ile Thr Gly Ala Gln Ala Glu Asp Glu Ala Asp Tyr Tyr Cys Gln Ala
             95                 100                 105 tgg gac agc agt act gca gtg gta ttc ggc gga ggg acc aag ctg acc         387
Trp Asp Ser Ser Thr Ala Val Val Phe Gly Gly Gly Thr Lys Leu Thr
        110                 115                 120 gtc cta ggc ggt ggc gga tca ggt ggc ggt gga agt ggc ggt ggt ggg         435
Val Leu Gly Gly Gly Gly Ser Gly Gly Gly Gly Ser Gly Gly Gly Gly
125                 130                 135                 140 tct gga ggt ggg ggc agt cag gtg cag ctg gtg cag tct ggg gga ggc         483
Ser Gly Gly Gly Gly Ser Gln Val Gln Leu Val Gln Ser Gly Gly Gly
                145                 150                 155 ttg gta cag cct ggc agg tcc ctg aga ctc tca tgt gca gct tct gga         531
Leu Val Gln Pro Gly Arg Ser Leu Arg Leu Ser Cys Ala Ala Ser Gly
            160                 165                 170 ttc acc ttt gat gat tat gcc atg cac tgg gtc cgg caa gct cca ggg         579
Phe Thr Phe Asp Asp Tyr Ala Met His Trp Val Arg Gln Ala Pro Gly
                175                 180                 185 aag ggc ctg gag tgg gtc tca ggt att agt tgg aat agt ggt atc ata         627
Lys Gly Leu Glu Trp Val Ser Gly Ile Ser Trp Asn Ser Gly Ile Ile
        190                 195                 200 ggc tat gcg gac tct gtg aag ggc cga ttc acc atc tcc aga gac aac         675
Gly Tyr Ala Asp Ser Val Lys Gly Arg Phe Thr Ile Ser Arg Asp Asn
205                 210                 215                 220 gcc aag aac tcc ctg tat ctg caa atg aac agt ctg aga gct gag gac         723
Ala Lys Asn Ser Leu Tyr Leu Gln Met Asn Ser Leu Arg Ala Glu Asp
                225                 230                 235 acg gcc ttg tat tac tgt gca aaa gat ctg agc agc agc tgg tac ggt         771
Thr Ala Leu Tyr Tyr Cys Ala Lys Asp Leu Ser Ser Ser Trp Tyr Gly
            240                 245                 250 gct ttt gat atc tgg ggc caa ggg aca atg gtc acc gtc tcg agc ggg         819
Ala Phe Asp Ile Trp Gly Gln Gly Thr Met Val Thr Val Ser Ser Gly
                255                 260                 265 ggt cat cat cac cac cac cac tag tga gaattc                              852
Gly His His His His His His
        270                 275

<210> SEQ ID NO 4
<211> LENGTH: 275
<212> TYPE: PRT
<213> ORGANISM: Artificial Sequence
<220> FEATURE:
<223> OTHER INFORMATION: Synthetic Sequence - MSLNH2a021LHscFv

<400> SEQUENCE: 4

Met Ala Ser Phe Pro Leu Leu Thr Leu Leu Thr His Cys Ala Gly
 1               5                  10                  15

Ser Trp Ala Ser Ser Glu Leu Thr Gln Asp Pro Ala Val Ser Val Ala
                 20                  25                  30

Leu Gly Gln Thr Val Arg Ile Thr Cys Gln Gly Asp Ser Leu Arg Ser
             35                  40                  45
```

```
Tyr Tyr Ala Ser Trp Tyr Gln Gln Lys Pro Gly Gln Ala Pro Val Leu
        50                  55                  60

Val Ile Tyr Gly Lys Asn Asn Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Gln Ala Trp Asp Ser Ser
            100                 105                 110

Thr Ala Val Val Phe Gly Gly Thr Lys Leu Thr Val Leu Gly Gly
            115                 120                 125

Gly Gly Ser Gly Gly Gly Gly Ser Gly Gly Gly Ser Gly Gly
130                 135                 140

Gly Ser Gln Val Gln Leu Val Gln Ser Gly Gly Gly Leu Val Gln Pro
145                 150                 155                 160

Gly Arg Ser Leu Arg Leu Ser Cys Ala Ala Ser Gly Phe Thr Phe Asp
                165                 170                 175

Asp Tyr Ala Met His Trp Val Arg Gln Ala Pro Gly Lys Gly Leu Glu
            180                 185                 190

Trp Val Ser Gly Ile Ser Trp Asn Ser Gly Ile Ile Gly Tyr Ala Asp
            195                 200                 205

Ser Val Lys Gly Arg Phe Thr Ile Ser Arg Asp Asn Ala Lys Asn Ser
210                 215                 220

Leu Tyr Leu Gln Met Asn Ser Leu Arg Ala Glu Asp Thr Ala Leu Tyr
225                 230                 235                 240

Tyr Cys Ala Lys Asp Leu Ser Ser Ser Trp Tyr Gly Ala Phe Asp Ile
                245                 250                 255

Trp Gly Gln Gly Thr Met Val Thr Val Ser Ser Gly Gly His His His
            260                 265                 270

His His His
    275

<210> SEQ ID NO 5
<211> LENGTH: 855
<212> TYPE: DNA
<213> ORGANISM: Artificial Sequence
<220> FEATURE:
<223> OTHER INFORMATION: Synthetic Sequence - MSLNH2a064LHscFv
<220> FEATURE:
<221> NAME/KEY: CDS
<222> LOCATION: (16)..(849)

<400> SEQUENCE: 5
aagcttgccg ccacc atg gcc agc ttc cct ctc ctc ctc acc ctc ctc act      51
              Met Ala Ser Phe Pro Leu Leu Leu Thr Leu Leu Thr
                1               5                   10 cac tgt gca gga tcc tgg gcc tcc tat gag ctg act cag cca ccc tcg      99
His Cys Ala Gly Ser Trp Ala Ser Tyr Glu Leu Thr Gln Pro Pro Ser
        15                  20                  25 gtg tca gtg tcc cca gga cag acg gcc agg atc acc tgc tct gga gat     147
Val Ser Val Ser Pro Gly Gln Thr Ala Arg Ile Thr Cys Ser Gly Asp
30                  35                  40 gca ttg cca aag cac tat gct tct tgg tac cag cag aag cca ggc cag     195
Ala Leu Pro Lys His Tyr Ala Ser Trp Tyr Gln Gln Lys Pro Gly Gln
45                  50                  55                  60 gcc cct gtc ctg ctg ata tat aaa gac act gag agg ccc tca ggg atc     243
Ala Pro Val Leu Leu Ile Tyr Lys Asp Thr Glu Arg Pro Ser Gly Ile
                65                  70                  75
```

```
cct gag cga ttc tct ggc tcc agc tca ggg aca aca gtc acg ttg acc      291
Pro Glu Arg Phe Ser Gly Ser Ser Ser Gly Thr Thr Val Thr Leu Thr
            80                  85                  90 atc agt gga gtc cag gca gaa gac gag gct gac tat tac tgt caa tca      339
Ile Ser Gly Val Gln Ala Glu Asp Glu Ala Asp Tyr Tyr Cys Gln Ser
        95                 100                 105 gcc gac agc agt gtt act gtg gta ttc ggc gga ggg acc aag ctg acc      387
Ala Asp Ser Ser Val Thr Val Val Phe Gly Gly Gly Thr Lys Leu Thr
    110                 115                 120 gtc cta ggc ggt gga gga tca ggt ggc ggt gga agt ggc ggt ggt ggg      435
Val Leu Gly Gly Gly Gly Ser Gly Gly Gly Gly Ser Gly Gly Gly Gly
125                 130                 135                 140 tct gga ggt ggg ggc agt cag gtg cag ctg gtg caa tct ggg gga ggc      483
Ser Gly Gly Gly Gly Ser Gln Val Gln Leu Val Gln Ser Gly Gly Gly
                145                 150                 155 ttg gta cag cct ggc agg tcc ctg aga ctc tcc tgt gca gcc tct gga      531
Leu Val Gln Pro Gly Arg Ser Leu Arg Leu Ser Cys Ala Ala Ser Gly
            160                 165                 170 ttc acc ttt gat gat tat gcc atg cac tgg gtc cgg caa gct cca ggg      579
Phe Thr Phe Asp Asp Tyr Ala Met His Trp Val Arg Gln Ala Pro Gly
        175                 180                 185 aag ggc ctg gag tgg gtc tca ggt att agt tgg aat agt ggt agc ata      627
Lys Gly Leu Glu Trp Val Ser Gly Ile Ser Trp Asn Ser Gly Ser Ile
    190                 195                 200 ggc tat gcg gac tct gtg aag ggc cga ttc acc atc tcc aga gac aac      675
Gly Tyr Ala Asp Ser Val Lys Gly Arg Phe Thr Ile Ser Arg Asp Asn
205                 210                 215                 220 gcc aag aac tcc ctg tat ctg caa atg aac agt ctg aga gct gag gac      723
Ala Lys Asn Ser Leu Tyr Leu Gln Met Asn Ser Leu Arg Ala Glu Asp
            225                 230                 235 acg gcc ttg tat tac tgt gca aaa gat atc ggt agc agt ggc tgg tac      771
Thr Ala Leu Tyr Tyr Cys Ala Lys Asp Ile Gly Ser Ser Gly Trp Tyr
        240                 245                 250 ggg gct ttt gat atc tgg ggc caa ggg acc acg gtc acc gtc tcg agc      819
Gly Ala Phe Asp Ile Trp Gly Gln Gly Thr Thr Val Thr Val Ser Ser
    255                 260                 265 ggg ggt cat cat cac cac cac cac tag tga gaattc                       855
Gly Gly His His His His His His
        270                 275

<210> SEQ ID NO 6
<211> LENGTH: 276
<212> TYPE: PRT
<213> ORGANISM: Artificial Sequence
<220> FEATURE:
<223> OTHER INFORMATION: Synthetic Sequence - MSLNH2a064LHscFv

<400> SEQUENCE: 6

Met Ala Ser Phe Pro Leu Leu Leu Thr Leu Leu Thr His Cys Ala Gly
1               5                   10                  15

Ser Trp Ala Ser Tyr Glu Leu Thr Gln Pro Pro Ser Val Ser Val Ser
            20                  25                  30

Pro Gly Gln Thr Ala Arg Ile Thr Cys Ser Gly Asp Ala Leu Pro Lys
        35                  40                  45

His Tyr Ala Ser Trp Tyr Gln Gln Lys Pro Gly Gln Ala Pro Val Leu
    50                  55                  60

Leu Ile Tyr Lys Asp Thr Glu Arg Pro Ser Gly Ile Pro Glu Arg Phe
65                  70                  75                  80

Ser Gly Ser Ser Ser Gly Thr Thr Val Thr Leu Thr Ile Ser Gly Val
                85                  90                  95
```

```
Gln Ala Glu Asp Glu Ala Asp Tyr Tyr Cys Gln Ser Ala Asp Ser Ser
                100                 105                 110

Val Thr Val Val Phe Gly Gly Gly Thr Lys Leu Thr Val Leu Gly Gly
            115                 120                 125

Gly Gly Ser Gly Gly Gly Ser Gly Gly Gly Ser Gly Gly Gly
130                 135                 140

Gly Ser Gln Val Gln Leu Val Gln Ser Gly Gly Gly Leu Val Gln Pro
145                 150                 155                 160

Gly Arg Ser Leu Arg Leu Ser Cys Ala Ala Ser Gly Phe Thr Phe Asp
                165                 170                 175

Asp Tyr Ala Met His Trp Val Arg Gln Ala Pro Gly Lys Gly Leu Glu
            180                 185                 190

Trp Val Ser Gly Ile Ser Trp Asn Ser Gly Ser Ile Gly Tyr Ala Asp
        195                 200                 205

Ser Val Lys Gly Arg Phe Thr Ile Ser Arg Asp Asn Ala Lys Asn Ser
    210                 215                 220

Leu Tyr Leu Gln Met Asn Ser Leu Arg Ala Glu Asp Thr Ala Leu Tyr
225                 230                 235                 240

Tyr Cys Ala Lys Asp Ile Gly Ser Ser Gly Trp Tyr Gly Ala Phe Asp
                245                 250                 255

Ile Trp Gly Gln Gly Thr Thr Val Thr Val Ser Ser Gly Gly His His
            260                 265                 270

His His His His
275
```

```
<210> SEQ ID NO 7
<211> LENGTH: 849
<212> TYPE: DNA
<213> ORGANISM: Artificial Sequence
<220> FEATURE:
<223> OTHER INFORMATION: Synthetic Sequence - MSLNH2a006LHscFv
<220> FEATURE:
<221> NAME/KEY: CDS
<222> LOCATION: (16)..(843)

<400> SEQUENCE: 7
aagcttgccg ccacc atg gcc agc ttc cct ctc ctc ctc acc ctc ctc act      51
               Met Ala Ser Phe Pro Leu Leu Leu Thr Leu Leu Thr
                 1               5                  10 cac tgt gca gga tcc tgg gcc tcc tat gag ctg aca cag cca ccc tcg       99
His Cys Ala Gly Ser Trp Ala Ser Tyr Glu Leu Thr Gln Pro Pro Ser
         15                  20                  25 gtg tca gtg tcc cca gga cag acg gcc agg atc acc tgc tct gga gat      147
Val Ser Val Ser Pro Gly Gln Thr Ala Arg Ile Thr Cys Ser Gly Asp
     30                  35                  40 gca ttg cca aag caa tat gct tat tgg tac cag cag aag cca ggc cag      195
Ala Leu Pro Lys Gln Tyr Ala Tyr Trp Tyr Gln Gln Lys Pro Gly Gln
45                  50                  55                  60 gcc cct gtg ctg gtg ata tat aaa gac agt gag agg ccc tca ggg atc      243
Ala Pro Val Leu Val Ile Tyr Lys Asp Ser Glu Arg Pro Ser Gly Ile
                 65                  70                  75 cct gag cga ttc tct ggc tcc agc tca ggg aca aca gtc acg ttg acc      291
Pro Glu Arg Phe Ser Gly Ser Ser Ser Gly Thr Thr Val Thr Leu Thr
             80                  85                  90 atc agt gga gtc cag gca gaa gac gag gct gac tat tac tgt caa tca      339
Ile Ser Gly Val Gln Ala Glu Asp Glu Ala Asp Tyr Tyr Cys Gln Ser
         95                 100                 105 gca gac agc agt ggt act gtg gta ttc ggc gga ggg acc aag ctg acc      387
```

```
                Ala Asp Ser Ser Gly Thr Val Val Phe Gly Gly Thr Lys Leu Thr
                    110                 115                 120 gtc ctg ggc ggt ggc gga tca ggt ggc ggt gga agt ggc ggt ggt ggg              435
Val Leu Gly Gly Gly Gly Ser Gly Gly Gly Gly Ser Gly Gly Gly Gly
125                 130                 135                 140 tct gga ggt ggg ggc agt gag gtg cag ctg gtg cag tct ggg gga ggc              483
Ser Gly Gly Gly Gly Ser Glu Val Gln Leu Val Gln Ser Gly Gly Gly
                145                 150                 155 ttg gta cag cct ggc agg tcc ctg aga ctc tcc tgt gca gcc tct gga              531
Leu Val Gln Pro Gly Arg Ser Leu Arg Leu Ser Cys Ala Ala Ser Gly
            160                 165                 170 ttc acc ttt gat gat tat gcc atg cac tgg gtc cgg caa gct cca ggg              579
Phe Thr Phe Asp Asp Tyr Ala Met His Trp Val Arg Gln Ala Pro Gly
        175                 180                 185 aag ggc ctg gag tgg gtc tca ggt att agt tgg aat agt ggt agc ata              627
Lys Gly Leu Glu Trp Val Ser Gly Ile Ser Trp Asn Ser Gly Ser Ile
    190                 195                 200 gtc tat gcg gac tct gtg aag ggc cga ttc acc atc tcc aga gac aac              675
Val Tyr Ala Asp Ser Val Lys Gly Arg Phe Thr Ile Ser Arg Asp Asn
205                 210                 215                 220 gcc aag aac tcc ctg tat ctg caa atg aac agt ctg aga gct gag gac              723
Ala Lys Asn Ser Leu Tyr Leu Gln Met Asn Ser Leu Arg Ala Glu Asp
                225                 230                 235 acg gcc ttg tat tac tgt gca aaa gac cgc agc agc tgg tac ggg ggg              771
Thr Ala Leu Tyr Tyr Cys Ala Lys Asp Arg Ser Ser Trp Tyr Gly Gly
            240                 245                 250 ttt gac tac tgg ggc cag gga acc ctg gtc acc gtc tcg agc ggg ggt              819
Phe Asp Tyr Trp Gly Gln Gly Thr Leu Val Thr Val Ser Ser Gly Gly
        255                 260                 265 cat cat cac cac cac cac tag tga gaattc                                       849
His His His His His His
    270

<210> SEQ ID NO 8
<211> LENGTH: 274
<212> TYPE: PRT
<213> ORGANISM: Artificial Sequence
<220> FEATURE:
<223> OTHER INFORMATION: Synthetic Sequence - MSLNH2a006LHscFv

<400> SEQUENCE: 8

Met Ala Ser Phe Pro Leu Leu Leu Thr Leu Leu Thr His Cys Ala Gly
1               5                   10                  15

Ser Trp Ala Ser Tyr Glu Leu Thr Gln Pro Pro Ser Val Ser Val Ser
            20                  25                  30

Pro Gly Gln Thr Ala Arg Ile Thr Cys Ser Gly Asp Ala Leu Pro Lys
        35                  40                  45

Gln Tyr Ala Tyr Trp Tyr Gln Gln Lys Pro Gly Gln Ala Pro Val Leu
    50                  55                  60

Val Ile Tyr Lys Asp Ser Glu Arg Pro Ser Gly Ile Pro Glu Arg Phe
65                  70                  75                  80

Ser Gly Ser Ser Ser Gly Thr Thr Val Thr Leu Thr Ile Ser Gly Val
                85                  90                  95

Gln Ala Glu Asp Glu Ala Asp Tyr Tyr Cys Gln Ser Ala Asp Ser Ser
            100                 105                 110

Gly Thr Val Val Phe Gly Gly Gly Thr Lys Leu Thr Val Leu Gly Gly
        115                 120                 125

Gly Gly Ser Gly Gly Gly Gly Ser Gly Gly Gly Gly Ser Gly Gly Gly
    130                 135                 140
```

```
Gly Ser Glu Val Gln Leu Val Gln Ser Gly Gly Leu Val Gln Pro
145                 150                 155                 160

Gly Arg Ser Leu Arg Leu Ser Cys Ala Ala Ser Gly Phe Thr Phe Asp
                165                 170                 175

Asp Tyr Ala Met His Trp Val Arg Gln Ala Pro Gly Lys Gly Leu Glu
            180                 185                 190

Trp Val Ser Gly Ile Ser Trp Asn Ser Gly Ser Ile Val Tyr Ala Asp
        195                 200                 205

Ser Val Lys Gly Arg Phe Thr Ile Ser Arg Asp Asn Ala Lys Asn Ser
210                 215                 220

Leu Tyr Leu Gln Met Asn Ser Leu Arg Ala Glu Asp Thr Ala Leu Tyr
225                 230                 235                 240

Tyr Cys Ala Lys Asp Arg Ser Ser Trp Tyr Gly Gly Phe Asp Tyr Trp
                245                 250                 255

Gly Gln Gly Thr Leu Val Thr Val Ser Ser Gly Gly His His His His
            260                 265                 270

His His

<210> SEQ ID NO 9
<211> LENGTH: 864
<212> TYPE: DNA
<213> ORGANISM: Artificial Sequence
<220> FEATURE:
<223> OTHER INFORMATION: Synthetic Sequence - MSLNH2a059LHscFv
<220> FEATURE:
<221> NAME/KEY: CDS
<222> LOCATION: (16)..(858)

<400> SEQUENCE: 9
aagcttgccg ccacc atg gcc agc ttc cct ctc ctc ctc acc ctc ctc act          51
                Met Ala Ser Phe Pro Leu Leu Leu Thr Leu Leu Thr
                 1               5                  10 cac tgt gca gga tcc tgg gcc tcc tat gag ctg atg cag cca ccc tcg          99
His Cys Ala Gly Ser Trp Ala Ser Tyr Glu Leu Met Gln Pro Pro Ser
         15                  20                  25 gtg tca gtg tcc cca gga cag acg gcc agg atc acc tgc tct gga gat         147
Val Ser Val Ser Pro Gly Gln Thr Ala Arg Ile Thr Cys Ser Gly Asp
 30                  35                  40 gca ttg cca aag caa tat gct tat tgg tac cag cag aag cca ggc cag         195
Ala Leu Pro Lys Gln Tyr Ala Tyr Trp Tyr Gln Gln Lys Pro Gly Gln
 45                  50                  55                  60 gcc cct gtg ctg gtg ata tat aaa gac agt gag agg ccc tca ggg atc         243
Ala Pro Val Leu Val Ile Tyr Lys Asp Ser Glu Arg Pro Ser Gly Ile
                 65                  70                  75 cct gag cga ttc tct ggc tcc agc tca ggg aca aca gtc acg ttg acc         291
Pro Glu Arg Phe Ser Gly Ser Ser Ser Gly Thr Thr Val Thr Leu Thr
             80                  85                  90 atc agt gga gtc cag gca gaa gac gag gct gac tat tac tgt caa tca         339
Ile Ser Gly Val Gln Ala Glu Asp Glu Ala Asp Tyr Tyr Cys Gln Ser
         95                 100                 105 gca gac agc agt ggt act tat aga gat gtg gta ttc ggc gga ggg acc         387
Ala Asp Ser Ser Gly Thr Tyr Arg Asp Val Val Phe Gly Gly Gly Thr
     110                 115                 120 aag ctg acc gtc cta ggc ggt ggc gga tca ggt ggc ggt gga agt ggc         435
Lys Leu Thr Val Leu Gly Gly Gly Gly Ser Gly Gly Gly Gly Ser Gly
125                 130                 135                 140 ggt ggt ggg tct gga ggt ggg ggc agt gag gtg cag ctg gtg cag tct         483
Gly Gly Gly Ser Gly Gly Gly Gly Ser Glu Val Gln Leu Val Gln Ser
                145                 150                 155
```

```
ggg gga ggc ttg gta cag cct ggc agg tcc ctg aga ctc tcc tgt gca      531
Gly Gly Gly Leu Val Gln Pro Gly Arg Ser Leu Arg Leu Ser Cys Ala
        160                 165                 170 gcc tct gga ttc acc ttt gat gat tat gcc atg cac tgg gtc cgg caa      579
Ala Ser Gly Phe Thr Phe Asp Asp Tyr Ala Met His Trp Val Arg Gln
    175                 180                 185 gct cca ggg aag ggc ctg gag tgg gtc tca ggt att agt tgg aat agt      627
Ala Pro Gly Lys Gly Leu Glu Trp Val Ser Gly Ile Ser Trp Asn Ser
190                 195                 200 ggt agc ata ggc tat gcg gac tct gtg aag ggc cga ttc acc atc tcc      675
Gly Ser Ile Gly Tyr Ala Asp Ser Val Lys Gly Arg Phe Thr Ile Ser
205                 210                 215                 220 aga gac aac gcc aag aac tcc ctg tat ctg caa atg aac agt ctg aga      723
Arg Asp Asn Ala Lys Asn Ser Leu Tyr Leu Gln Met Asn Ser Leu Arg
                225                 230                 235 gct gag gac acg gcc ttg tat tac tgt gca aaa ggt ctg ggt agt agt      771
Ala Glu Asp Thr Ala Leu Tyr Tyr Cys Ala Lys Gly Leu Gly Ser Ser
            240                 245                 250 ggt tat tac gac gct ttt gat atc tgg ggc caa ggg acc acg gtc acc      819
Gly Tyr Tyr Asp Ala Phe Asp Ile Trp Gly Gln Gly Thr Thr Val Thr
                255                 260                 265 gtc tcg agc ggg ggt cat cat cac cac cac cac tag tga gaattc           864
Val Ser Ser Gly Gly His His His His His His
            270                 275

<210> SEQ ID NO 10
<211> LENGTH: 279
<212> TYPE: PRT
<213> ORGANISM: Artificial Sequence
<220> FEATURE:
<223> OTHER INFORMATION: Synthetic Sequence - MSLNH2a059LHscFv

<400> SEQUENCE: 10

Met Ala Ser Phe Pro Leu Leu Thr Leu Leu Thr His Cys Ala Gly
1               5                   10                  15

Ser Trp Ala Ser Tyr Glu Leu Met Gln Pro Ser Val Ser Val Ser
                20                  25                  30

Pro Gly Gln Thr Ala Arg Ile Thr Cys Ser Gly Asp Ala Leu Pro Lys
            35                  40                  45

Gln Tyr Ala Tyr Trp Tyr Gln Gln Lys Pro Gly Gln Ala Pro Val Leu
        50                  55                  60

Val Ile Tyr Lys Asp Ser Glu Arg Pro Ser Gly Ile Pro Glu Arg Phe
65                  70                  75                  80

Ser Gly Ser Ser Ser Gly Thr Thr Val Thr Leu Thr Ile Ser Gly Val
                85                  90                  95

Gln Ala Glu Asp Glu Ala Asp Tyr Tyr Cys Gln Ser Ala Asp Ser Ser
            100                 105                 110

Gly Thr Tyr Arg Asp Val Val Phe Gly Gly Gly Thr Lys Leu Thr Val
        115                 120                 125

Leu Gly Gly Gly Gly Ser Gly Gly Gly Ser Gly Gly Gly Gly Ser
    130                 135                 140

Gly Gly Gly Gly Ser Glu Val Gln Leu Val Gln Ser Gly Gly Gly Leu
145                 150                 155                 160

Val Gln Pro Gly Arg Ser Leu Arg Leu Ser Cys Ala Ala Ser Gly Phe
                165                 170                 175

Thr Phe Asp Asp Tyr Ala Met His Trp Val Arg Gln Ala Pro Gly Lys
            180                 185                 190
```

```
Gly Leu Glu Trp Val Ser Gly Ile Ser Trp Asn Ser Gly Ser Ile Gly
            195                 200                 205

Tyr Ala Asp Ser Val Lys Gly Arg Phe Thr Ile Ser Arg Asp Asn Ala
        210                 215                 220

Lys Asn Ser Leu Tyr Leu Gln Met Asn Ser Leu Arg Ala Glu Asp Thr
225                 230                 235                 240

Ala Leu Tyr Tyr Cys Ala Lys Gly Leu Gly Ser Ser Gly Tyr Tyr Asp
                245                 250                 255

Ala Phe Asp Ile Trp Gly Gln Gly Thr Thr Val Thr Val Ser Ser Gly
            260                 265                 270

Gly His His His His His His
        275

<210> SEQ ID NO 11
<211> LENGTH: 858
<212> TYPE: DNA
<213> ORGANISM: Artificial Sequence
<220> FEATURE:
<223> OTHER INFORMATION: Synthetic Sequence - MSLNH2b011LHscFv
<220> FEATURE:
<221> NAME/KEY: CDS
<222> LOCATION: (16)..(852)

<400> SEQUENCE: 11
```

| | | |
|---|---|---|
| aagcttgccg ccacc atg gcc agc ttc cct ctc ctc ctc acc ctc ctc act<br>                   Met Ala Ser Phe Pro Leu Leu Leu Thr Leu Leu Thr<br>                   1              5                 10 | | 51 |
| cac tgt gca gga tcc tgg gcc cag gca ggg ctg act cag cca ccc tcg<br>His Cys Ala Gly Ser Trp Ala Gln Ala Gly Leu Thr Gln Pro Pro Ser<br>        15                  20                 25 | | 99 |
| gtg tca gtg tcc cca gga cag acg gcc agg atc acc tgc tct gga gat<br>Val Ser Val Ser Pro Gly Gln Thr Ala Arg Ile Thr Cys Ser Gly Asp<br>30                   35                  40 | | 147 |
| gca ttg cca aag caa ttt act tat tgg tac cag cag aag cca ggc cag<br>Ala Leu Pro Lys Gln Phe Thr Tyr Trp Tyr Gln Gln Lys Pro Gly Gln<br>45                   50                  55                 60 | | 195 |
| gcc cct gtg ttg gtg ata tat caa gac cgt gag agg ccc tca ggg atc<br>Ala Pro Val Leu Val Ile Tyr Gln Asp Arg Glu Arg Pro Ser Gly Ile<br>                 65                  70               75 | | 243 |
| cct gag cga ttc tct ggc tcc agc tca ggg aca aaa gtc acg ttg acc<br>Pro Glu Arg Phe Ser Gly Ser Ser Ser Gly Thr Lys Val Thr Leu Thr<br>                 80                  85               90 | | 291 |
| atc agt gga gtc cag gca gaa gac gag gct gac tat tat tgt caa tca<br>Ile Ser Gly Val Gln Ala Glu Asp Glu Ala Asp Tyr Tyr Cys Gln Ser<br>                 95                  100              105 | | 339 |
| gca gac agc agt ggt act tat cgg gtg ttc ggc gga ggg acc aag ctg<br>Ala Asp Ser Ser Gly Thr Tyr Arg Val Phe Gly Gly Gly Thr Lys Leu<br>          110                 115              120 | | 387 |
| acc gtc cta ggc ggt ggc gga tca ggt ggc ggt gga agt ggc ggt ggt<br>Thr Val Leu Gly Gly Gly Gly Ser Gly Gly Gly Gly Ser Gly Gly Gly<br>125                  130              135              140 | | 435 |
| ggg tct gga ggt ggg ggc agt gag gtg cag ctg gtg gag tct ggg gga<br>Gly Ser Gly Gly Gly Gly Ser Glu Val Gln Leu Val Glu Ser Gly Gly<br>                  145                  150               155 | | 483 |
| ggc ttg gta cag cct ggc agg tcc ctg aga ctc tcc tgt gca gcc tct<br>Gly Leu Val Gln Pro Gly Arg Ser Leu Arg Leu Ser Cys Ala Ala Ser<br>                 160                  165              170 | | 531 |
| gga ttc acc ttt gat gat tat gcc atg cac tgg gtc cgg caa gct cca<br>Gly Phe Thr Phe Asp Asp Tyr Ala Met His Trp Val Arg Gln Ala Pro<br>          175                 180                 185 | | 579 |

```
ggg aag ggc ctg gag tgg gtc tca ggt att agt tgg aat agt ggt agc      627
Gly Lys Gly Leu Glu Trp Val Ser Gly Ile Ser Trp Asn Ser Gly Ser
    190             195                 200 ata ggc tat gcg gac tct gtg aag ggc cga ttc acc atc tcc aga gac      675
Ile Gly Tyr Ala Asp Ser Val Lys Gly Arg Phe Thr Ile Ser Arg Asp
205                 210                 215                 220 aac gcc aag aac tcc ctg tat ctg caa atg aac agt ctg aga gct gag      723
Asn Ala Lys Asn Ser Leu Tyr Leu Gln Met Asn Ser Leu Arg Ala Glu
                225                 230                 235 gac acg gcc ttg tat tac tgt gca aaa gat gcg ggt agt agt ggt tat      771
Asp Thr Ala Leu Tyr Tyr Cys Ala Lys Asp Ala Gly Ser Ser Gly Tyr
            240                 245                 250 tgg agc tac ttt gac tac tgg ggc cag ggc acc ctg gtc acc gtc tcg      819
Trp Ser Tyr Phe Asp Tyr Trp Gly Gln Gly Thr Leu Val Thr Val Ser
                255                 260                 265 agc ggg ggt cat cat cac cac cac cac tag tga gaattc                   858
Ser Gly Gly His His His His His His
    270                 275
```

<210> SEQ ID NO 12
<211> LENGTH: 277
<212> TYPE: PRT
<213> ORGANISM: Artificial Sequence
<220> FEATURE:
<223> OTHER INFORMATION: Synthetic Sequence - MSLNH2b011LHscFv

<400> SEQUENCE: 12

```
Met Ala Ser Phe Pro Leu Leu Leu Thr Leu Leu Thr His Cys Ala Gly
1               5                   10                  15

Ser Trp Ala Gln Ala Gly Leu Thr Gln Pro Ser Val Ser Val Ser
            20                  25                  30

Pro Gly Gln Thr Ala Arg Ile Thr Cys Ser Gly Asp Ala Leu Pro Lys
                35                  40                  45

Gln Phe Thr Tyr Trp Tyr Gln Gln Lys Pro Gly Gln Ala Pro Val Leu
            50                  55                  60

Val Ile Tyr Gln Asp Arg Glu Arg Pro Ser Gly Ile Pro Glu Arg Phe
65                  70                  75                  80

Ser Gly Ser Ser Ser Gly Thr Lys Val Thr Leu Thr Ile Ser Gly Val
                85                  90                  95

Gln Ala Glu Asp Glu Ala Asp Tyr Tyr Cys Gln Ser Ala Asp Ser Ser
            100                 105                 110

Gly Thr Tyr Arg Val Phe Gly Gly Gly Thr Lys Leu Thr Val Leu Gly
                115                 120                 125

Gly Gly Gly Ser Gly Gly Gly Gly Ser Gly Gly Gly Gly Ser Gly Gly
            130                 135                 140

Gly Gly Ser Glu Val Gln Leu Val Glu Ser Gly Gly Gly Leu Val Gln
145                 150                 155                 160

Pro Gly Arg Ser Leu Arg Leu Ser Cys Ala Ala Ser Gly Phe Thr Phe
                165                 170                 175

Asp Asp Tyr Ala Met His Trp Val Arg Gln Ala Pro Gly Lys Gly Leu
            180                 185                 190

Glu Trp Val Ser Gly Ile Ser Trp Asn Ser Gly Ser Ile Gly Tyr Ala
                195                 200                 205

Asp Ser Val Lys Gly Arg Phe Thr Ile Ser Arg Asp Asn Ala Lys Asn
            210                 215                 220

Ser Leu Tyr Leu Gln Met Asn Ser Leu Arg Ala Glu Asp Thr Ala Leu
225                 230                 235                 240
```

-continued

```
Tyr Tyr Cys Ala Lys Asp Ala Gly Ser Ser Gly Tyr Trp Ser Tyr Phe
            245                 250                 255

Asp Tyr Trp Gly Gln Gly Thr Leu Val Thr Val Ser Ser Gly Gly His
            260                 265                 270

His His His His His
            275
```

ANTI-MESOTHELIN POLYPEPTIDE, AND TUMOR IMAGING AGENTS AND COMPLEXES THEREOF

CROSS-REFERENCE TO RELATED APPLICATIONS

This patent application is the U.S. national phase of International Patent Application No. PCT/JP2018/012391, filed on Mar. 27, 2018, which claims the benefit of Japanese Patent Application No. 2017-210508, filed on Oct. 31, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 41,159 bytes ASCII (Text) file named "749228Sequence-Listing.txt," created Apr. 28, 2020.

TECHNICAL FIELD

The present invention relates to a DNA, a polypeptide, an anti-mesothelin antibody, a tumor imaging agent, and a complex.

BACKGROUND ART

Mesothelin (MSLN) is a 40-kDa glycoprotein that is attached to the membrane via a GPI anchor. Normally, MSLN is expressed locally in the mesothelium of the pleurae, peritoneum, and pericardium. However, MSLN is known to be highly expressed in many cancer cells of, for example, mesothelioma, ovarian cancer, pancreatic cancer, colorectal cancer, and breast cancer in cancerous tissues (Non-patent Literatures 1 to 2).

MSLN is first synthesized as a full-length 71-kDa precursor protein and then cleaved by a proteolytic enzyme such as furin to yield a 31-kDa polypeptide called "megakaryocyte potentiating factor" (MPF) and a 40-kDa polypeptide that is attached to the cell membrane via a GPI anchor, i.e., mature MSLN. Further, it has been reported that some GPI-anchored MSLN is separated from the cell membrane and released (soluble MSLN). As a function of MSLN, involvement in cell adhesion and proliferation has been reported.

Under such circumstances, MSLN is promising as a target molecule for cancer diagnosis and treatment, and many antibodies that recognize MSLN, such as MORAb-009 (amatuximab) and HN1, have been prepared and reported to date (Non-patent Literatures 3 to 5, and Patent Literatures 1 to 2).

CITATION LIST

Patent Literature

PTL 1: JP2014-221064A
PTL 2: JP2011-504372A

Non-Patent Literature

NPL 1: Eur. J. Cancer 44, 46-53, 2008
NPL 2: Clin. Cancer Res. 10, 3937-3942, 2004
NPL 3: Lung Cancer, 68:455-459, 2010
NPL 4: Int. J. Cancer, 128: 2020-30, 2011
NPL 5: Scientific Reports 5:09928, 2015

SUMMARY OF INVENTION

Technical Problem

An object of the present invention is to provide a novel polypeptide, DNA, anti-mesothelin antibody, complex, and tumor imaging agent that are effective for cancer diagnosis and treatment.

Solution to Problem

The present invention provides the following DNA, polypeptide, anti-mesothelin antibody, tumor imaging agent, and complex.

Item 1. A DNA comprising any of (a) to (c):
(a) a DNA comprising any of the base sequences of
positions 16 to 831 of SEQ ID NO: 1,
positions 16 to 822 of SEQ ID NO: 3,
positions 16 to 825 of SEQ ID NO: 5,
positions 16 to 819 of SEQ ID NO: 7,
positions 16 to 834 of SEQ ID NO: 9, and
positions 16 to 828 of SEQ ID NO: 11;
(b) a DNA encoding a polypeptide comprising any of the amino acid sequences of
positions 1 to 272 of SEQ ID NO: 2,
positions 1 to 269 of SEQ ID NO: 4,
positions 1 to 270 of SEQ ID NO: 6,
positions 1 to 268 of SEQ ID NO: 8,
positions 1 to 273 of SEQ ID NO: 10, and
positions 1 to 271 of SEQ ID NO: 12; and
(c) a complementary strand of the DNA (a) or (b).

Item 2. A polypeptide comprising any of the amino acid sequences of
positions 1 to 272 of SEQ ID NO: 2,
positions 1 to 269 of SEQ ID NO: 4,
positions 1 to 270 of SEQ ID NO: 6,
positions 1 to 268 of SEQ ID NO: 8,
positions 1 to 273 of SEQ ID NO: 10, and
positions 1 to 271 of SEQ ID NO: 12.

Item 3. An anti-mesothelin antibody comprising any of the amino acid sequences of
positions 1 to 272 of SEQ ID NO: 2,
positions 1 to 269 of SEQ ID NO: 4,
positions 1 to 270 of SEQ ID NO: 6,
positions 1 to 268 of SEQ ID NO: 8,
positions 1 to 273 of SEQ ID NO: 10, and
positions 1 to 271 of SEQ ID NO: 12.

Item 4. A tumor imaging agent comprising the polypeptide according to Item 2.

Item 5. The tumor imaging agent according to Item 4, further comprising $^{89}Zr$.

Item 6. The tumor imaging agent according to Item 4 or 5, which is for imaging a tumor expressing mesothelin.

Item 7. A complex in which the polypeptide according to Item 2 and an antitumor substance are linked.

Advantageous Effects of Invention

Since the anti-MSLN scFv of the present invention has a lower molecular weight and shows faster blood clearance than conventional full-length antibodies, the anti-MSLN scFv enables a tumor expressing MSLN to be specifically visualized in a short period of time in PET using radiolabeled scFv, compared with conventional full-length antibodies.

Moreover, the antibody, which has a low molecular weight, can be modified for targeting to an antitumor agent such as a polymeric micellar DDS preparation.

Further, the use of $^{89}$Zr, which is a PET nuclide that does not emit β-rays during decay, allows safer cancer imaging.

BRIEF DESCRIPTION OF DRAWINGS

In FIG. 3, black indicates each anti-human MSLN cp3-scFv antibody clone, and gray indicates an HR1 007 anti-habu-snake-venom scFv antibody used as a control. Clones framed in black were selected for their high reactivity found by FCM. The numerical values in FIG. 3 indicate the ratio of the mean fluorescence intensity (MEI) of each anti-human MSLN cp3-scFv antibody clone and the MFI of the HR1 007 anti-habu-snake-venom scFv antibody used as a control.

In FIG. 5, black indicates each anti-human MSLN His-tag scFv antibody clone, and gray indicates a control. The control uses only an anti-His-tag antibody as a secondary antibody without using an anti-human MSLN His-tag scFv antibody clone as a primary antibody. The lower graphs show FCM results obtained using full-length IgG mouse anti-human MSLN antibody 11-25. Black indicates results obtained using the full-length IgG mouse anti-human MSLN antibody, and gray indicates results obtained using an IgG isotype control anti-KLH antibody as a negative control. The numerical values in FIG. 5 indicate the ratio of the mean fluorescence intensity (MEI) of each anti-human MSLN cp3-scFv antibody clone or full-length IgG mouse anti-human MSLN antibody 11-25 to the MFI of the control.

FIG. 6 shows PET and CT images 3 hours after administration of the $^{89}$Zr-DFO-scFv antibodies that recognize human MSLM. H2a064 and H1a050 are the clone names of anti-human MSLN His-tag scFv antibodies.

In FIG. 7, the black columns indicate scFv clone Ha050, and the white columns indicate scFv clone H2a064. Error bars indicate SD (*p<0.01).

FIG. 9 shows the DNA sequence and amino acid sequence of MSLNH1a050LHscFv.

FIG. 11 shows PET and CT images obtained using (a) $^{89}$Zr-labeled trastuzumab and (b) $^{64}$Cu-labeled trastuzumab.

DESCRIPTION OF EMBODIMENTS

The present inventors previously developed an imaging technique for tumor cells using an IgG antibody having a relatively high affinity and specificity for mesothelin (MSLN), obtained by immunizing mice with MSLN protein. However, mouse antibodies are immunogenic when being administered to humans, and induce production of antibodies against the administered antibodies, making it difficult to administer them multiple times. In order to reduce antigenicity, the inventors have established an anti-mesothelin antibody derived from a human antibody gene.

The antibody used in the present invention is an scFv, which is a low-molecular-weight antibody in which only variable regions of heavy and light chains of an antibody are connected with a short linker.

Figure 4:
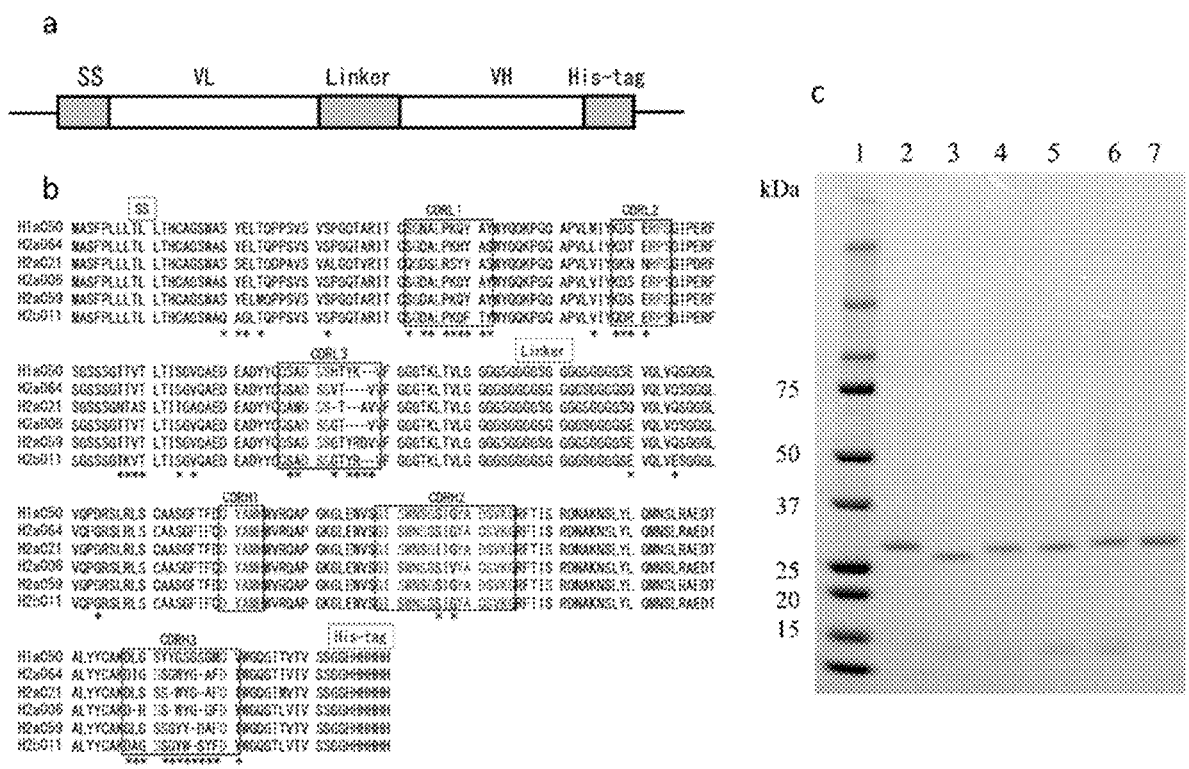
FIG. 4. Structure of the obtained anti-human MSLN His-tag-scFv antibodies and analysis by SDS-PAGE. a. Structure of anti-human MSLN His-tag-scFv antibody. b. Amino acid sequence of anti-human MSLN His-tag-scFv antibody. Complementarity determining regions (CDRs) of the light and heavy chain variable regions are shown in boxes. Asterisks indicate amino acid residues that differ among the clones, and red letters indicate amino acid residues that remain unchanged in the CDR regions. The His-tag is composed of six histidine residues. SS indicates a signal sequence. The complementarity determining regions (CDRs) were estimated based on data of V BASE (The MRC Centre for Protein Engineering, MRC Laboratory of Molecular Biology). c. 100 mM dithiothreitol (DTT) was used for reducing samples for reduced SDS-PAGE analysis of His-tag-scFv antibody clones. Lane 1: molecular size marker, Lane 2: His-Tag-scFv H1a050 (27064.24 Da), Lane 3: His-Tag-scFv H2a064 (26683.87 Da), Lane 4: His-Tag-scFv H2a021 (26708.96 Da), Lane 5: His-Tag-scFv H2a006 (26701.85 Da), Lane 6: His-Tag-scFv H2a059 (27124.32 Da), and Lane 7: His-Tag-scFv H2b011 (27033.18 Da). The molecular weights were all calculated from the amino acid sequences.

The anti-mesothelin scFv antibody of the present invention is a polypeptide comprising any of positions 1 to 272 of SEQ ID NO: 2, positions 1 to 269 of SEQ ID NO: 4, positions 1 to 270 of SEQ ID NO: 6, positions 1 to 268 of SEQ ID NO: 8, positions 1 to 273 of SEQ ID NO: 10, and positions 1 to 271 of SEQ ID NO: 12. A tag, such as a His tag, a protein tag (e.g., GST or MBP), a HA tag, a myc tag, or a FLAG tag, may be attached to this polypeptide to facilitate purification. Moreover, the polypeptide of the present invention also encompasses those having any peptide bound to its N-terminal or C-terminal side. The peptides of SEQ ID NOs: 2, 4, 6, 8, 10, 12 of the present invention are shown in FIG. 4b.

SEQ ID NOs: 1 and 2 are derived from scFv clone H1a050, SEQ ID NOs: 3 and 4 are derived from scFv clone H2a021, SEQ ID NOs: 5 and 6 are derived from scFv clone H2a064, SEQ ID NOs: 7 and 8 are derived from scFv clone H2a006, SEQ ID NOs: 9 and 10 are derived from scFv clone H2a059, and SEQ ID NOs: 11 and 12 are derived from scFv clone H2b011.

FIG. 9 shows a preferred scFv antibody of the present invention.

The DNA of the present invention encodes the peptide of the present invention and encompasses (a) a DNA comprising any of the base sequences of positions 16 to 831 of SEQ ID NO: 1, positions 16 to 822 of SEQ ID NO: 3, positions 16 to 825 of SEQ ID NO: 5, positions 16 to 819 of SEQ ID NO: 7, positions 16 to 834 of SEQ ID NO: 9, and positions 16 to 828 of SEQ ID NO: 11, (b) a DNA encoding a polypeptide comprising any of the amino acid sequences of positions 1 to 272 of SEQ ID NO: 2, positions 1 to 269 of SEQ ID NO: 4, positions 1 to 270 of SEQ ID NO: 6, positions 1 to 268 of SEQ ID NO: 8, positions 1 to 273 of SEQ ID NO: 10, and positions 1 to 271 of SEQ ID NO: 12, and (c) a complementary strand of DNA (a) or (b) above.

SEQ ID NOs: 1, 3, 5, 7, 9, and 11 contain a HindIII recognition sequence and a Kozak sequence added at the 5' end and an EcoRI recognition sequence at the 3' end; however, in place of these sequences or in addition to these sequences, any sequence may be added. For example, the DNA of the present invention encompasses vectors incorporating any of the base sequences of positions 16 to 831 of SEQ ID NO: 1, positions 16 to 822 of SEQ ID NO: 3, positions 16 to 825 of SEQ ID NO: 5, positions 16 to 819 of SEQ ID NO: 7, positions 16 to 834 of SEQ ID NO: 9, and positions 16 to 828 of SEQ ID NO: 11.

The polypeptide of the present invention can be obtained by transforming cells with a vector containing the DNA of the present invention, and culturing the transformed cells. Examples of cells for producing the polypeptide of the present invention include eukaryotic cells such as yeasts, insect cells (insect cell/baculovirus expression system), and mammalian cells (e.g., CHO); prokaryotic cells such as *Escherichia coli* and *Bacillus subtilis*; and archaea. CHO is preferable.

The polypeptide of the present invention can be labeled with a labeling substance. Examples of labeling substances include $^{89}$Zr, $^{99m}$Tc, $^{111}$In, $^{113m}$In, $^{67}$Ga, $^{68}$Ga, $^{201}$Tl, $^{51}$Cr, $^{57}$Co, $^{58}$Co, $^{60}$Co, $^{85}$Sr, $^{197}$Hg, $^{64}$Cu, $^{123}$I, $^{125}$I, $^{124}$I, $^{131}$I, $^{90}$Y, $^{177}$Lu, $^{186}$Re, $^{188}$Re, $^{211}$At, $^{225}$Ac, $^{213}$Bi, $^{212}$Pb, $^{166}$Ho, $^{44}$Sc, $^{47}$Sc, $^{227}$Th, and like radionuclides, fluorescein, rhodamine, cyanine dye, Alexa Fluor, quantum dots, Texas Red, indocyanine green (ICG), and like fluorescent materials. $^{89}$Zr is preferable.

The complex of the present invention comprises the polypeptide of the present invention and an antitumor substance. Examples of antitumor substances include anticancer agents, polymeric micellar DDS preparations, and the like. Examples of anticancer agents include, but are not limited to, doxorubicin, daunorubicin, cisplatin, oxaliplatin, carboplatin, paclitaxel, irinotecan, SN-38, actinomycin D, vincristine, vinblastine, methotrexate, azathioprine, fluorouracil, mitomycin C, docetaxel, cyclophosphamide, capecitabine, epirubicin, gemcitabine, mitoxantrone, leucovorin, vinorelbine, trastuzumab, etoposide, estramustine, prednisone, interferon α, interleukin-2, bleomycin, ifosfamide, mesna, altretamine, topotecan, cytarabine, methylprednisolone, dexamethasone, mercaptopurine, thioguanine, fludarabine, gemtuzumab, idarubicin, tretinoin, alemtuzumab, chlorambucil, cladribine, imatinib, dacarbazine, procarbazine, mechlorethamine, rituximab, denileukin diftitox, trimethoprim/sulfamethoxazole, allopurinol, carmustine, tamoxifen, filgrastim, temozolomide, melphalan, vinorelbine, azacitidine, thalidomide, mitomycin, and the like.

The tumor to be imaged in the present invention is not particularly limited as long as it is a tumor expressing mesothelin. Examples of such include small-cell lung cancer, non-small-cell lung cancer, pancreatic cancer, prostate cancer, cervical cancer, cancer of the corpus uteri, ovarian cancer, breast cancer, gastric cancer, and the like.

The tumor imaging agent of the present invention can be used for PET, SPECT, CT, or MRI imaging alone or in combination (e.g., PET and CT; SPECT and CT; or SPECT, CT, and PET).

EXAMPLES

The present invention is further illustrated by the following examples, which should not be construed as further limiting.

Example 1

I Materials and Methods
(1) Reagents

Deferoxamine-p-SCN (DFO) was purchased from Macrocyclics (Dallas, TX). A PD-10 desalting column was purchased from GE Healthcare (Uppsala, Sweden). Amicon Ultra 0.5 centrifugal filter units were purchased from Merck Millipore (Billerica, MA). Other reagents were special-grade reagents.

(2) Preparation of Anti-Human MSLN-scFv

Figure 1:
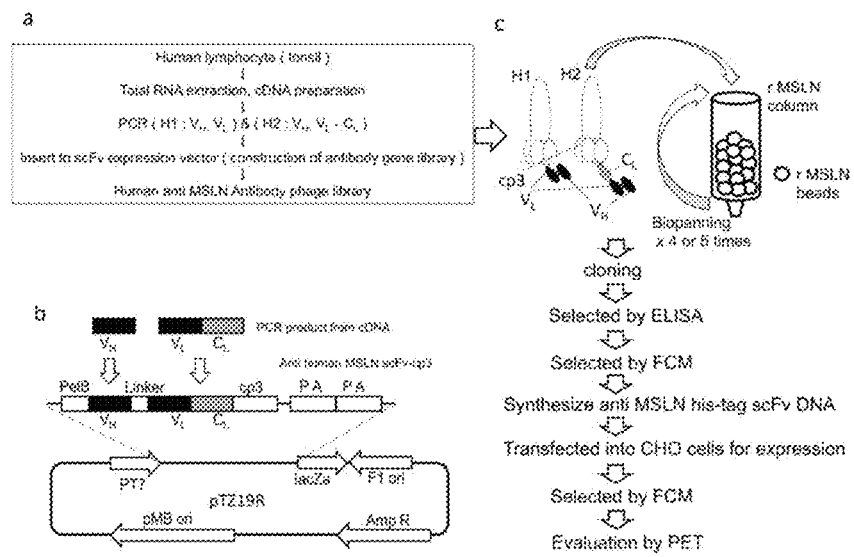
FIG. 1. Schematic diagrams of preparation of an anti-human MSLN scFv antibody and structure of an anti-human MSLN scFv-cp3 antibody. a. Scheme for preparation of a human naive antibody phage library. A library was prepared using human tonsil lymphocytes. b. Structure of an scFv antibody with a cp3 sequence. The antibody has a structure in which PelB and cp3 sequences are added to variable regions of heavy and light chains joined by a linker and a light chain constant region. PT7 indicates a T7 promoter. The variable regions are shown as black squares, and the constant region is shown as a gray square. c. Scheme for concentration and selection of an scFv antibody with a cp3 sequence (cp3-scFv) and preparation of an scFv antibody with His-tag sequence. cp3-scFv antibodies were concentrated by performing biopanning four to five times with a column (r-MSLN column) using beads (r-MSLN beads) to which human recombinant MSLN was bound via a His-tag (Dynabeads (registered trademark) His-tag Isolation & Pulldown: 10103D; Invitrogen), or a mouse monoclonal anti-His-tag antibody (MEL: M136-3) and protein G (Dynabeads (registered trademark) protein G: 100.04D; Invitrogen). After concentration, the individual cp3-scFv antibodies were cloned, and their binding ability to MSLN was evaluated by enzyme-linked immunosorbent assay (ELISA). The binding ability of scFv antibodies found to show a relatively high activity by ELISA to cancer cells was examined by flow cytometry (FCM), and five highly reactive clones were selected. Based on sequence information regarding the selected scFvs, DNA of each scFv antibody with the His-tag sequence added to it was synthesized and expressed in Chinese hamster ovary (CHO) cells, and the ability to bind to cancer cells was examined by FCM. scFv antibodies with the His-tag sequence added to them that were found to be highly reactive by FCM were evaluated by PET imaging. $V_H$ indicates a heavy chain variable region, $V_L$ indicates a light chain variable region, and $C_L$ indicates a light chain constant region. The variable regions were shown in black, and the constant region is shown in gray.
Figure 2:
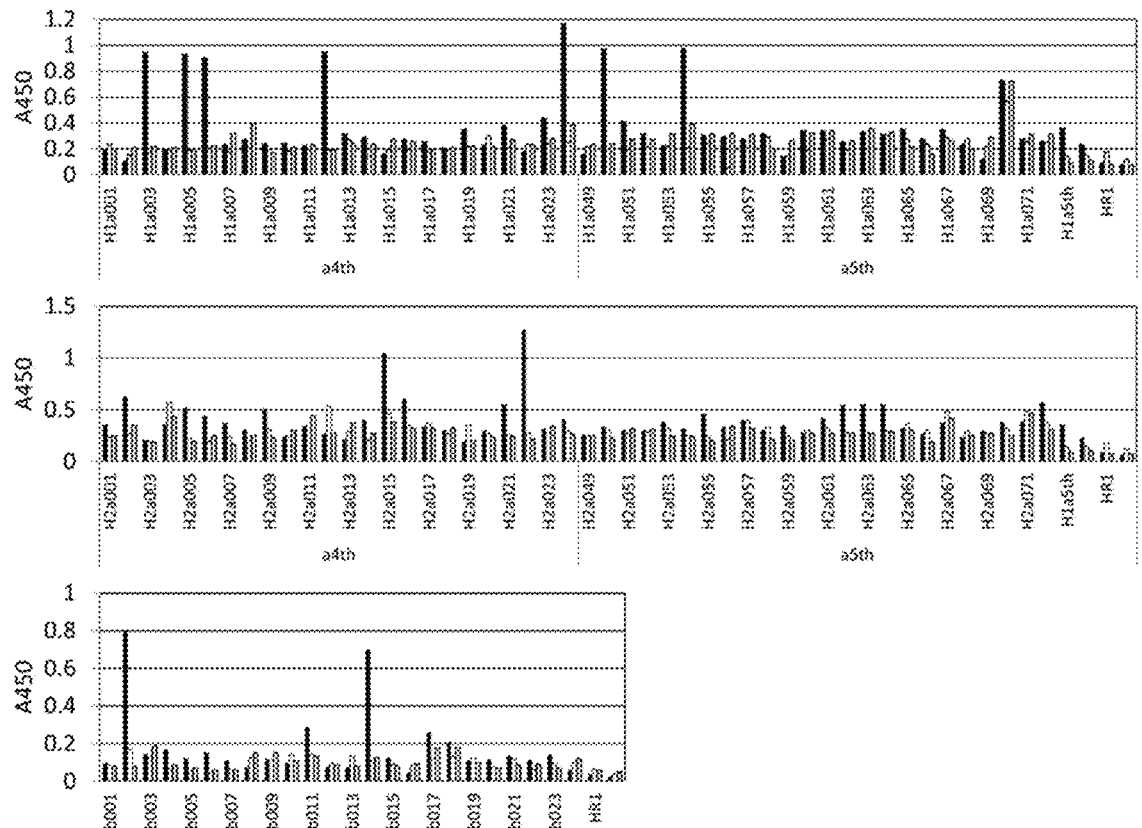
FIG. 2. Selection of cp3-scFv clones and evaluation by ELISA. To evaluate the specificity of cp3-scFvs for r-MSLN, r-MSLN was immobilized on 96-well plates and used for ELISA. The absorbance is indicated on the y-axis, and the names of clones are indicated on the x-axis (because of limited space, every other clone name is written). The black bars indicate the reactivity of the cp3-scFv clones to immobilized r-MSLN, and the white bars indicate the reactivity of the cp3-scFv clones when EGFR was immobilized on plates as a negative control. The gray bars indicate the reactivity of the cp3-scFv clones to only PBS when r-MSLN was not immobilized on plates. The terms "4th" and "5th" in the upper and middle graphs in FIG. 2 indicate the number of times panning was performed. The term "4th" indicates clones obtained after concentration by performing panning four times, and the term "5th" indicates clones obtained after concentration by performing panning five times. When panning is performed four times, panning is performed using beads in which antigen r-MSLN is bound to Dynabeads (registered trademark) His-tag Isolation & Pulldown (10103D) ("His-tag beads") twice, and panning is then performed using beads in which antigen r-MSLN is bound to a mouse monoclonal anti-His-tag antibody (MBL: M136-3) attached to Dynabeads (registered trademark) protein G (100.04D: invitrogen) ("PG beads") twice. When panning is performed five times, panning is further performed using His-tag beads after performing panning four times. The lower graph shows clones obtained by further performing panning using PG beads after performing panning four times. HR1 is a pc3-scFv specific for habu snake venom used as a control.

Total RNA was extracted from palatine tonsil lymphocytes of patients with tonsillar hypertrophy and inflammation, and cDNA was obtained by reverse transcription using primers for $V_H$, $V_L$, and $V_L$-$C_L$ sequences according to a standard method. Expression signal PelB and phage cp3 sequences were added to the obtained sequences. The $V_H$ and $V_L$-$C_L$ sequences, and the $V_H$ and $V_L$ sequences were connected by a $(G_4S)_3$ linker, and introduced into *Escherichia coli* (DH12S) using pTZ19R phagemid vector (Thermo Fisher scientific, Massachusetts, USA). The *Escherichia coli* was infected with M13KO7 helper phage, thereby preparing a human naive antibody phage library (FIG. 1a and FIG. 1b). An scFv composed of the $V_H$ and $V_L$ sequences was designated as H1, and an scFv-CL composed of the $V_H$ and $V_L$-$C_L$ sequences was designated as H2 (FIG. 1c). Preparation of recombinant MSLN ("r-MSLN") used for scFv concentration and enzyme-linked immunosorbent assay (ELISA) was as disclosed in a document of Iwahori et al. (Iwahori K. et al., Lung Cancer. 2008; 62(1): 45-54). The obtained H1 scFv-cp3 and H2 scFv-cp3 were concentrated by performing panning four to five times with a column packed with beads to which r-MSLN was bound, and specific affinity for MSLN was examined by ELISA using a plate on which r-MSLN was immobilized (FIG. 2). The phages were cloned by infecting *Escherichia coli* to form colonies on a plate medium, and the gene sequence of each clone was confirmed with a DNA sequencer. The obtained human MSLN-scFv-cp3 clones were subjected to selection based on reactivity to r-MSLN by ELISA using immobilized r-MSLN. The reactivity of the scFv-cp3 clones selected by ELISA to MSLN expressed in cancer cells was further examined by FCM using cell lines with high MSLN expression and a cell line with low MSLN expression (FIG. 3). scFv genes with a His-tag sequence were synthesized from the DNA sequences of the selected highly reactive scFv-cp3 clones, and scFvs were expressed using mammalian cells. FIG. 1c shows an overall flow of production of the humanized anti-human MSLN-scFvs. This study was approved by the Ethics Committee of Okayama University and the Ethics Committee of Medical & Biological Laboratories Co., Ltd., and was implemented according to the ethical guidelines for human genome and gene research enacted by the Japanese Government and the Declaration of Helsinki.

(3) Selection of Anti-Human MSLN scFv-Cp3 by ELISA

Human r-MSLN and epidermal growth factor receptor (EGFR) as a negative control were individually dissolved in PBS at 5 μg/mL, dispensed in an amount of 50 μL into each well of 96-well MAXIsorp plates, and immobilized by incubation at 4° C. overnight. 200 μL of 2.5% BSA was added, and blocking was performed by incubation at room temperature for 2 hours. 50 μL of each anti-human MSLN scFv-cp3 clone was individually added, followed by incubation at room temperature for 1 hour. Thereafter, 50 μL of an anti-cp3 rabbit polyclonal antibody (5 μg/mL) was added, followed by incubation at room temperature for 1 hour. 50 μL of tertiary antibody Anti-IgG (H+L chain) (Rabbit) pAb-HRP (MBL 458, Nagoya, JAPAN) diluted 5000-fold with PBS was added, followed by incubation at room temperature for 1 hour. Subsequently, color was developed with 50 μL of 3,3',5,5'-tetramethylbenzidine, and the absorbance at 450 nm was measured with a microplate reader.

(4) Preparation of Anti-Human MSLN-scFv-His Tag

With a view to clinical application, scFvs expressed in mammalian cells were produced. Artificial genes in which a linker and a His-tag were added to the $V_H$ and $V_L$ sequences of each anti-MSLN scFv-cp3 selected by ELISA and FCM were synthesized, and each gene was individually inserted into mammalian cell expression vector pCx17.4 (Lonza, San Francisco, CA, USA) and transfected into CHOK1-GSKO (FIG. 4a and FIG. 4b). Each anti-human MSLN-scFv-His-tag was purified in such a manner that the culture supernatant was applied to a 1-mL Ni-NTA agarose (QIAGEN) column, washed with PBS, and eluted with 200 mM imidazole (3 mL, 4 times), and the whole amount was dialyzed against PBS overnight and concentrated by ultrafiltration (Amicon). Each purified anti-human MSLN-scFv-His-tag was confirmed by SDS-PAGE. Precision Plus Protein™ Prestained Standard Dual Color (Bio-rad, California, USA) was used as a molecular weight marker (FIG. 4c). Furthermore, the molecular weight was measured with MALDI-TOF-MS (AXIMA (registered trademark) Performance, Shimadzu, Kyoto, Japan).

(5) Cell Culture

Cancer cell lines established from various tissues were obtained from American Type Culture Collection (ATCC) and JCRB cell bank. As media, RPMI-1640, EMEM, DMEM, and IMDM were basically used according to the data sheet of each kind of cells; 10 to 20% fetal bovine serum (FBS) was added thereto, supplements, such as insulin and a nonessential amino acid (NEAA), were added in necessary amounts depending on the cells, and 1% penicillin/streptomycin was added to all of the media. The media, supplements, etc. were purchased from Gibco/Life Technologies (CA, USA). Table 1 shows the names of cell lines, tissue origins, disease names, and the like. Culture was performed at 37° C. in an incubator humidified with 5% carbon dioxide.

TABLE 1

Examination of MSLN expression in each cancer cell type by flow cytometry

| name | source | tissue | disease | MSLN exp ref | MSLN exp FCM |
|---|---|---|---|---|---|
| NCI-N87 | ATCC | stomach; derived from metastatic site: liver | gastric carcinoma | +[43] | ++ |
| MKN45 | JCRB | Stomach; derived from metastatic: liver | adenocarcinoma, poorly differentiated | +[44] | + |
| MKN74 | JCRB | Stomach; derived from metastatic: liver | stomach cancer | +[44, 45] | + |
| NCI-H226 | ATCC | lung; derived from metastatic site: pleural effusion | squamous cell carcinoma; mesothelioma | +[33, 45, 46, 47, 48] | ++ |
| NCI-H596 | ATCC | lung | adenosquamous carcinoma | +[49] | + |
| NCI-H520 | ATCC | lung | squamous cell carcinoma | −[33] | − |
| ChaGo-K-1 | ATCC | lung, bronchus | bronchogenic carcinoma | | − |
| BxPC-3 | ATCC | pancreas | adenocarcinoma | +[33, 50, 51] | + |
| CFPAC-1 | ATCC | pancreas; derived from metastatic: liver | ductal adenocarcinoma; cystic fibrosis | +[33] | + |
| PANC-1 | ATCC | pancreas/duct | epithelioid carcinoma | +[50] or −[33, 51, 52] | − |
| OVCAR-3 | ATCC | ovary | adenocarcinoma | +[1, 2, 12, 13, 47] | ++ |
| SK-OV-3 | ATCC | ovary | adenocarcinoma | +[2, 50, 53] | + |
| SiHa | ATCC | cervix | squamous cell carcinoma | | ++ |
| Hela | ATCC | cervix | adenocarcinoma | +[1, 53, 54] | + |
| HEC-1-A | JCRB | uterus | Human endometroid adenocarcinoma | | + |
| HEC-50B | JCRB | uterus | endometrioid adenocarcinoma | | − |
| Ishikawa | JCRB | uterus | endometrioid adenocarcinoma | | − |
| 22Rv1 | ATCC | prostate | carcinoma | | + |
| A431 | ATCC | skin/epidermis | epidermoid carcinoma | −[12, 47, 48, 55] | − |
| TNB1 | JCRB | neural | Neuroblastoma | | − |
| T98G | JCRB | neural | glioblastoma | | − |
| MEG-01 | ATCC | hemo-lymphocytic | cronic leukemia | | − |
| Daudi | ATCC | Peripheral Blood | Burkitt's Lymphoma | | − |
| Jurkat | ATCC | Peripheral Blood | Acute T Cell Leukemia | −[56] | − |
| MCF-7 | ATCC | mammary gland, breast; derived from metastatic site: pleural effusion | adenocarcinoma | −[1] | − |
| HEP-G2 | JCRB | liver | Hepatoblastoma | −[12] | − |
| ACHN | ATCC | kidney; derived from metastatic site: pleural effusion | renal cell adenocarcinoma | | − |

Table 1 shows cell lines, tissues, diseases, and MSLN expression levels. The cell lines include three gastric cancer cell lines, four lung cancer cell lines (including bronchus), three pancreatic cancer cell lines, two ovarian cancer cell lines, two cervical cancer cell lines, three cell lines of cancer of the corpus uteri, one prostate cancer cell line, one colorectal cancer cell line, one skin cancer cell line, one neuroblastoma cell line, one glial cell line, three leukemia cell lines, one breast cancer cell line, one liver cancer cell line, and one kidney cancer cell line.

A total of 28 cell lines were used for FCM analysis. The "MSLN exp ref" column indicates positive MSLN expression shown in previous studies. The "MSLN exp FCM" column indicates the ratio of the mean fluorescence intensity (MEI) of scFv clone H1a050 in each MSLN-positive cancer cell line to the MIF of the control; a ratio of 5 or more was indicated as "++," a ratio of 4.9-1.5 was indicated as "+," and a ratio of 1.4 or less is indicated as "−."

(6) FCM Analysis of Antibodies

The human cancer cell lines (Table 1) were treated with Cell Dissociation Buffer, enzyme-free, PBS (Gibco/Life Technologies, CA, USA) and harvested as single-cell suspensions. 1×10$^6$ cells were washed once with cold PBS containing 2% FBS and 1 mM EDTA, and a full-length anti-human MSLN antibody, each anti-human MSLN cp3-scFv clone, or each His-tag scFv clone was used as a primary antibody. For the full-length anti-human MSLN antibody, an anti-KLH antibody (IgG2b isotype control) was used as a negative control, and an Alexa Fluor 488-labeled goat anti-mouse IgG antibody was used as a secondary antibody. For the anti-human MSLN cp3-scFvs, an antibody against hemorrhagic factor HR1-007 of habu snake venom was used as a negative control, and a rabbit anti-cp3 polyclonal antibody (MBL, Nagoya, Japan) was used as a secondary antibody. Further, an Alexa Fluor 488-labeled goat anti-rabbit polyclonal antibody (Invitrogen: A11034, USA) was used as a tertiary antibody. For the anti-human MSLN His-tag scFvs, an Alexa Fluor 488-labeled mouse anti-His-tag monoclonal antibody (No. D291-A48, MBL, Nagoya, JAPAN) was used as a secondary antibody. As a control, cells were treated without His-tag scFv. Finally, to sort dead cells, suspension in 100 µL of PBS containing 5 µL of 7-Amino-Actinomycin D (immunostep, Salamanca, Spain) (7AAD) and 1 mM EDTA was performed, followed by measurement using a BD FACSAria III flow cytometer (BD Biosciences, NJ, USA). Each antibody reaction was performed on ice for 1 hour, and washing was performed twice with 500 µL of PBS containing 2% FBS and 1 mM EDTA at each antibody reaction stage. The mean value of the fluorescence intensity (excluding the dead cell population) was obtained using BD FACS-Diva software and calculated using Microsoft Excel.

(7) DFO Modification and Radiolabeling for His-Tag scFv

DFO modification to each His-tag scFv was performed by incubation in bicarbonate buffer at a pH of 9.0 at 37° C. for 1 hour so that the ratio of dissolved chelating agent deferoxamine (p-SCN-Bn-DFO) to His-tag scFv was 3:1. $^{89}$Zr was produced with a cyclotron (HM-12 cyclotron, Sumitomo Heavy Industries Ltd., Tokyo, Japan), and $^{89}$Zr-oxalate was obtained. $^{89}$Zr-oxalate, Na$_2$CO$_3$ (2M), and HEPES (0.5 M) were mixed so that the ratio of $^{89}$Zr-oxalate to Na$_2$CO$_3$ (2M) to HEPES (0.5 M) was 2:1:10 and adjusted to a pH of 7.0, and the mixture was mixed with each DFO-modified His-tag scFv clone in which the solvent was replaced with gentisic acid physiological saline (5 mg/mL), followed by incubation at 37° C. for 30 minutes, thereby obtaining $^{89}$Zr-DFO-scFvs. Unbound $^{89}$Zr was removed by ultrafiltration using an Amicon Ultra 10K centrifugal filter. The radiochemical purity was determined by thin-layer chromatography-autoradiography (TLC-ARG) and HPLC (LC-20, Shimadzu Co., Kyoto, Japan). In TLC-ARG, each sample was spotted on a silica gel pate (silica gel, 60 RP-18F254S, Millipore), and this was developed using 50 mM EDTA (pH 5.0) as a mobile phase. HPLC was performed on a Superdex 200 10/300 column (10 mm×30 cm, GE Healthcare, Buckinghamshire, England) using D-PBS (Wako Pure Chemical Industries, Ltd.) (pH 7.0) as a mobile phase at a flow rate of 0.75 mL/min. The in vitro stability of the radiolabeled scFvs after incubation in 50% human plasma/PBS at 37° C. for 6 hours was also analyzed. Each $^{89}$Zr-DFO-scFv or anti-KLH scFv (50 µL) was added to 450 µL of mouse plasma. Immediately after mixing and after 6-hour incubation, a portion of the mixture of the radiolabeled scFv and plasma was measured at 230 nm by HPLC, and the radioactivity was measured with a GABI star (Raytest, Straubenhardt, Germany). Further, to evaluate changes in binding ability due to DFO modification and $^{89}$Zr labeling, the equilibrium dissociation constant ($K_D$) for antigen r-MSLN was measured with a BLItz intermolecular interaction analyzer (ForteBio, Inc., CA, USA) using Amine-Reactive Second Genelation (AR2G) biosensor probes.

(8) Model Animal

All animal experiments were conducted according to the guidelines of Okayama University and approved by the Animal Care and Use Committee, Okayama University (OKU-2013098). Five-week-old male BALB/c nu/nu mice were purchased from Charles River (Tokyo, Japan) and maintained under specific pathogen-free conditions at the Department of Animal Resources, Advanced Science Research Center, Okayama University, before use. For PET imaging, cultured cell line NCI-N87, which is positive for MSLN expression, and cultured cell line PANC-1, which is negative for MSLN expression, were individually cultured. 3×10$^6$ NCI-N87 cells were implanted into the right shoulder of the nude mice, and 1×10$^7$ PANC-1 cells were implanted into the left shoulder of the nude mice, to create tumor-bearing model mice. Imaging was carried out when the tumor size reached approximately 8 mm in diameter.

(9) Small Animal PET and CT Imaging

The mice with tumors formed from NCI-N87 and PANC-1 cell lines were anesthetized by inhalation of isoflurane. Each $^{89}$Zr-DFO-scFv was individually administered to the mice through their tail veins under anesthesia (n=3), and imaging was performed with a PET and CT system for medium-sized animals (Clairvivo PET, Shimadzu, Kyoto, Japan). Dynamic PET scanning was performed for 3 hours, and images were reconstructed using 3D-DRAMA. The average doses administered were as follows: H1a050 (6.0 MBq/8.3 µg) and H2a064 (4.1 MBq/11.5 µg). Before PET scanning, CT data were obtained using a CT scanner (Eminence Stargate, Shimadzu). PET and CT images were converted to DICOM format and fused using PMOD software version 3.3 (PMOD Technologies Ltd., Zurich, Switzerland). Three-dimensional volumes of interest (VOI) were drawn as tumors and blood pool on the PET and CT images in the heart to determine the mean percentage of the injected dose per gram of tissue (% ID/g). After CT scanning, all mice were euthanized for biodistribution studies. Tumors and major organs of the mice were collected and weighed, and the radioactivity in the organs was measured with a gamma counter (AccuFLEXγ7001, Hitachi Aloka Medical, Tokyo, Japan). Biodistribution data are expressed as % ID/g.

(10) Statistical Analysis

Data are presented as the mean±SD. Statistical analysis was carried out using an unpaired Student's t-test for comparison of two groups. P<0.05 was considered statistically significant.

II Results (1) Preparation and Selection of Anti-Human MSLN-scFv

Figure 3:
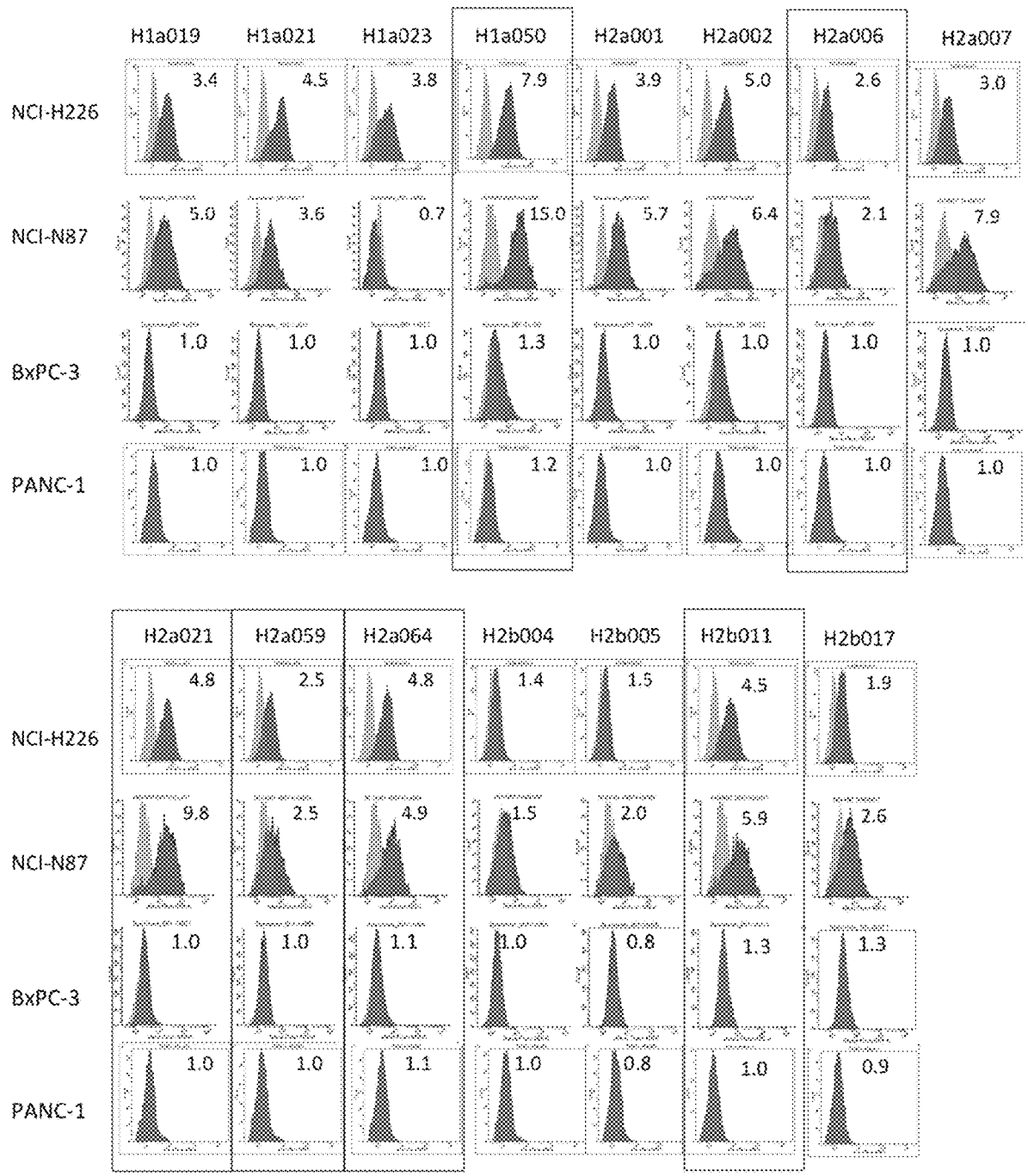
FIG. 3. Evaluation of anti-human MSLN cp3-scFv antibody clones by flow cytometry (FCM). The reactivity of anti-human MSLN cp3-scFv antibody clones was analyzed by FCM using lung cancer cells (NCI-H226), gastric cancer cells (NCI-N87), and pancreatic cancer cells (BxPC-3 and PANC-1).

An antibody phage library was prepared from cDNA of palatine tonsil lymphocytes of patients with tonsillar hypertrophy and inflammation, and biopanning was performed four to five times to obtain 120 anti-MSLN cp3-scFv clones. The reactivity of the obtained anti-MSLN cp3-scFv clones was examined by ELISA using immobilized r-MSLN, allowing selection of 15 scFv clones with high reactivity to r-MSLN. In selecting these 15 scFv clones, the gene sequence of each scFv clone was confirmed, and clones having similar sequences were not selected. Further, the reactivity of these anti-MSLN cp3-scFv clones was examined using cultured cancer cell lines. FCM analysis was performed using cell lines with high MSLN expression, i.e., lung cancer cell line NCI-H226, gastric cancer cell line NCI-N87, and pancreatic cancer cell line BxPC-3, and a cell line with extremely low MSLN expression, i.e., pancreatic cancer cell line PANC-1, as target cell lines. Through FCM analysis, six scFv clones with high reactivity to the cancer cells with high MSLN expression and low reactivity to the cancer cells with extremely low MSLN expression were selected (FIG. 3).

(2) Preparation and Selection of Anti-Human MSLN-scFv-His Tag

Figure 5:
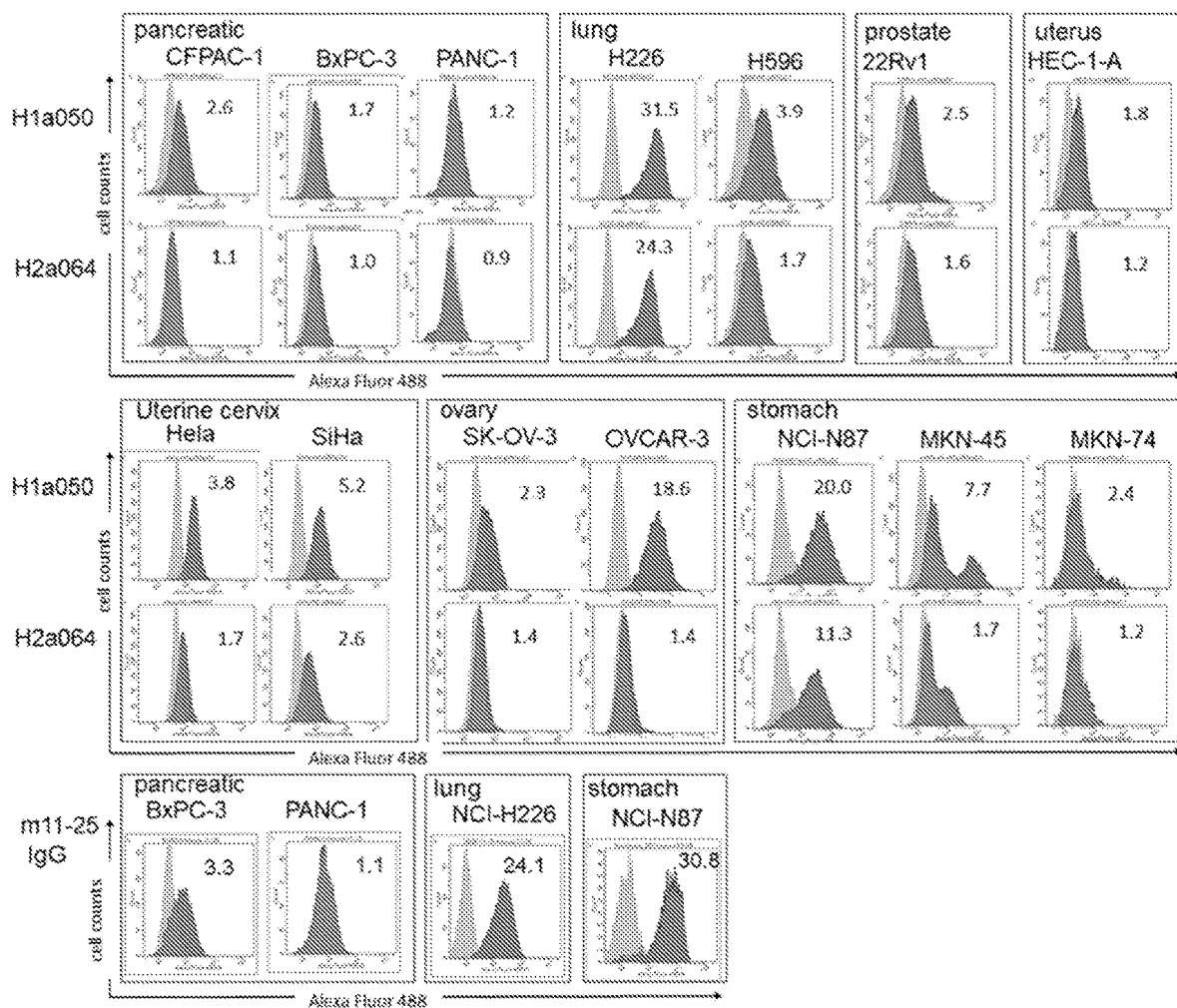
FIG. 5. Evaluation of anti-human MSLN His-tag scFv antibody clones using various cancer cell lines. The reactivity of anti-human MSLN His-tag scFv antibody clones to three kinds of pancreatic cancer cell lines, two kinds of lung cancer cell lines, one kind of prostate cancer cell line, one kind of cell line of cancer of the corpus uteri, two kinds of cervical cancer cell lines, two kinds of ovarian cancer cell lines, and three kinds of gastric cancer cell lines was analyzed by flow cytometry.

To prevent an scFv itself from serving as an antigen, scFvs were produced in mammalian cells. Specifically, anti-human MSLN-scFv-His-tag single-chain antibodies that can be produced in mammalian cells were prepared from the DNA sequences of the anti-MSLN cp3-scFv clones selected in (1) above by total gene synthesis, and each was individually inserted into a vector and introduced into CHO cells (FIG. 4a and FIG. 4b). Six scFv clones were prepared and analyzed by FCM using various cancer cell lines. Clones H1a050 and H2a064 showed a relatively high reactivity to MSLN-expressing cell lines. In particular, clone H1a050 also showed a relatively good reactivity to cancer cell lines established from various tissues (FIG. 5). Furthermore, H1a050 scFv showed reactivity similar to that of full-length anti-MSLN antibody 11-25 (FIG. 5). FIG. 4a shows the structure of anti-human MSLN His-tag scFv, and FIG. 4b shows the structure of the amino acid sequences of the six scFv clones. The molecular weights estimated from the DNA sequences and the molar extinction coefficients determined by calculation were as follows: His-tag scFv H1a050 (27063.24 Da, c=45130) and His-tag scFv H2a064 (26683.87 Da, c=49980). It was confirmed by SDS-PAGE that the His-tag anti-human MSLN scFv clones produced using CHO cells were prepared as scFvs having desired molecular weights (FIG. 4c). The molecular weights determined by analysis with MALDI-TOF-MS were as follows: His-tag scFv H1a050 (26926.58 Da) and His-tag scFv H2a064 (26547.88 Da). From the calculated values, it was confirmed that although there was a difference in molecular weight of approximately one amino acid residue, peptides having nearly desired molecular weights were obtained.

(3) DFO Modification and Radiolabeling for His-Tag scFv

The specific activity of DFO-modified His-tag scFvs after $^{89}$Zr labeling was as follows: H1a050 (0.496 MBq/μg) and H2a064 (0.365 MBq/μg). The in vitro stability of the $^{89}$Zr-labeled scFvs after 6-hour incubation in 50% human plasma at 37° C. was as follows: H1a050 (98.3%) and H2a064 (100%). Regarding the influence of DFO modification and $^{89}$Zr labeling on the binding ability of the scFvs, the equilibrium dissociation constant ($K_D$) of each scFv that was unlabeled, after DFO modification, or after $^{89}$Zr labeling was determined, and the results were as follows: H1a050 (4.68E−09, 3.38E−09, 4.62E−08) and H2a064 (5.96E−08, 1.14E−07, 7.82E−08). The unit was mol/L.

(4) Small Animal PET and CT Imaging I

Figure 6:
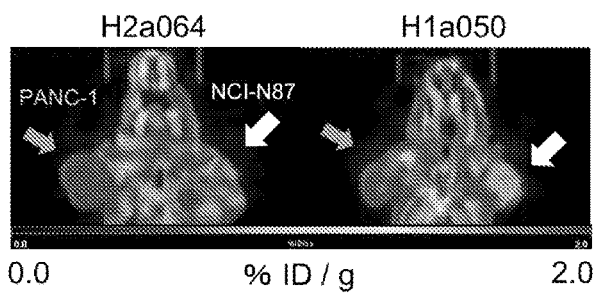
FIG. 6. PET and CT images obtained using $^{89}$Zr-DFO-scFv antibodies that recognize human MSLM in model mice. BALB/c nu/nu tumor-bearing mice have tumors from gastric cancer cell line MCI-N87 with high MSLN expression (right shoulder; white arrow) and pancreatic cancer cell line PANC-1 with low MSLN expression (left shoulder; blue arrow).
Figure 7:
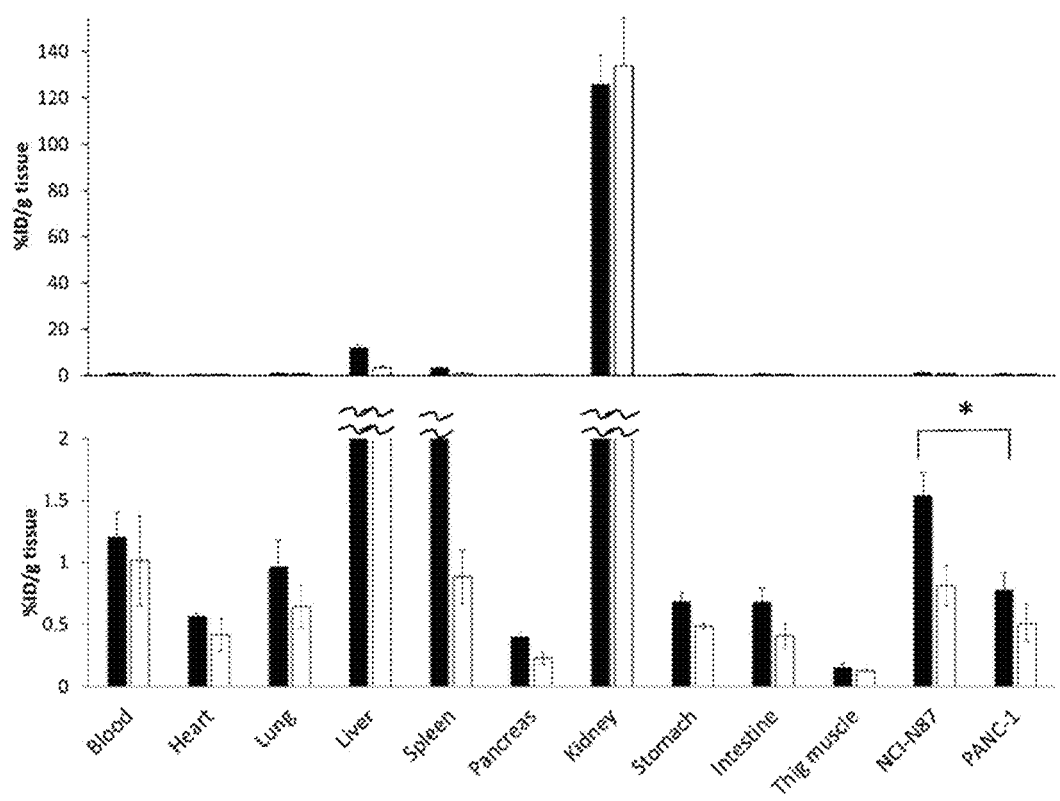
FIG. 7. Biodistribution of $^{89}$Zr-DFO-scFvs. Biodistribution 3 hours after intravenous injection of $^{89}$Zr-DFO-scFvs in tumor-bearing mice. Data were calculated as percentages of injection dose per gram (% ID/g tissue).

FIG. 6 shows PET and CT images 3 hours after administration of each $^{89}$Zr-labeled DFO-His-tag-scFv. Anti-human MSLN-scFv-His tag clones H1a050 and H2a064 both showed specific accumulation in the implanted tumor formed from NCI-N87, which is a cell line with high MSLN expression. In particular, clone H1a050 showed a higher accumulation than that of H2a064. FIG. 7 shows the biodistribution of the $^{89}$Z-labeled anti-human MSLN-scFv-His tag clones after PET and CT imaging. The results confirmed that $^{89}$Z-labeled H1a050 significantly more highly accumulated in the tumor derived from NCI-N87 than in the tumor derived from PANC-1. However, a relatively high accumulation of $^{89}$Zr (DFO-His-tag-scFv) in the kidneys and liver was also confirmed.

Figure 8:
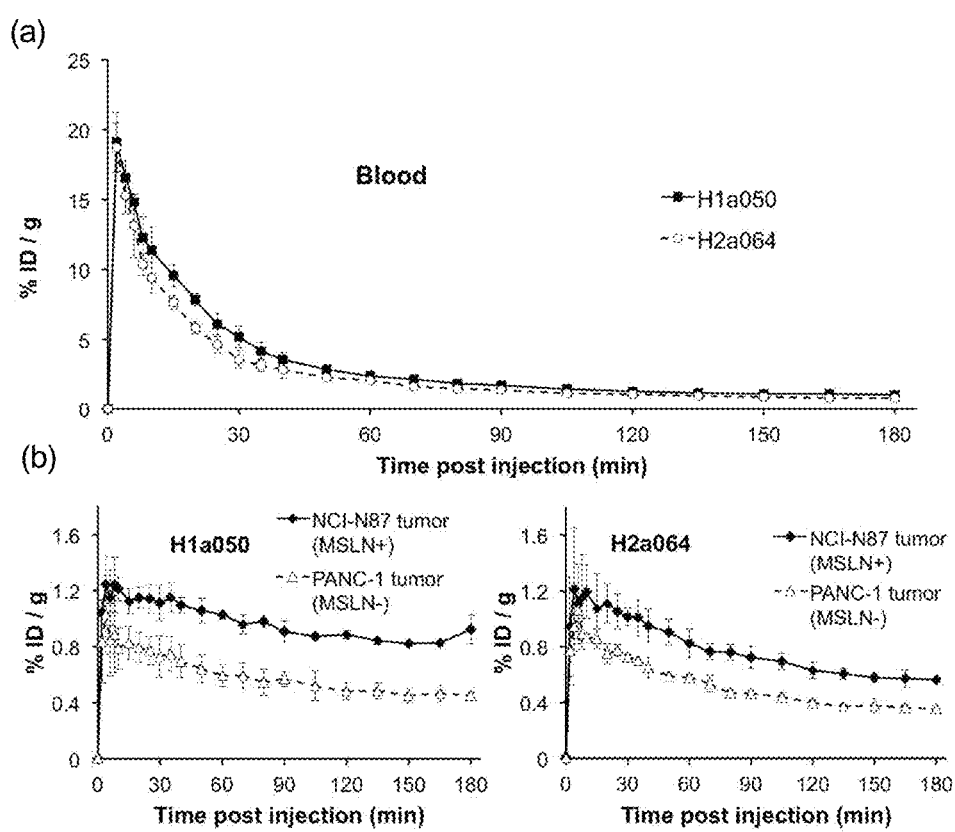
FIG. 8. Graphs of calculated accumulation of $^{89}$Zr-DFO-scFv antibodies in tumors and blood over time. (a) The y-axis shows accumulation of the antibodies in the blood. (b) Accumulation (% ID/g tissue) of the antibodies in tumors derived from a gastric cancer cell line with high MSLN expression (NCI-N87) and a pancreatic cancer cell line with low MSLN expression (PANC-1). Error bars in FIG. 8 indicate SD.

FIG. 8 shows graphs indicating changes over time in $^{89}$Z radioactivity in the blood, NCI-N87 tumor, and PANC-1 tumor obtained from PET images. From the data, uptake of the labeled antibodies into the blood and the tumors showing MSLN expression was confirmed from immediately after administration of the antibodies. The data showed that in contrast to rapid elimination in the blood, the $^{89}$Zr radioactivity in the tumors gradually decreased and was still retained at a high concentration even at 3 hours after administration.

The lower part of FIG. 8 shows graphs indicating changes over time in accumulation of the $^{89}$Zr-labeled scFvs in the tumor with low MSLN expression and the tumor with high MSLN expression. The radiolabeled anti-human MSLN-scFvs more highly accumulated in the NCI-N87 tumor than in the PANC-1 tumor. Further, the radioactivity of scFv clone H1a050 in the NCI-N87 tumor decreased slowly, compared with that of H2a064.

(5) Small Animal PET and CT Imaging II (i) Method $^{89}$Zr-DFO-1125-IgG (1 MBq/15 μg) was administered to mice with a tumor from NCI-N87 cell line through their tail veins (n=3), and imaging was performed with a PET system (Clairvivo PET, Shimadzu, Kyoto, Japan) immediately after each administration and 24, 48, 72, 96, and 144 hours after each administration. Images were reconstructed from the collected data using 3D-DRAMA. After PET scanning, CT data were obtained using a CT scanner (Eminence Stargate, Shimadzu). PET and CT images were converted to DICOM format and fused using PMOD software version 3.3 (PMOD Technologies Ltd., Zurich, Switzerland). Three-dimensional volumes of interest (VOI) were drawn as tumors and blood pool on the PET and CT images in the heart to determine the mean percentage of the injected dose per gram of tissue (% ID/g).

(ii) Results

Figure 10:
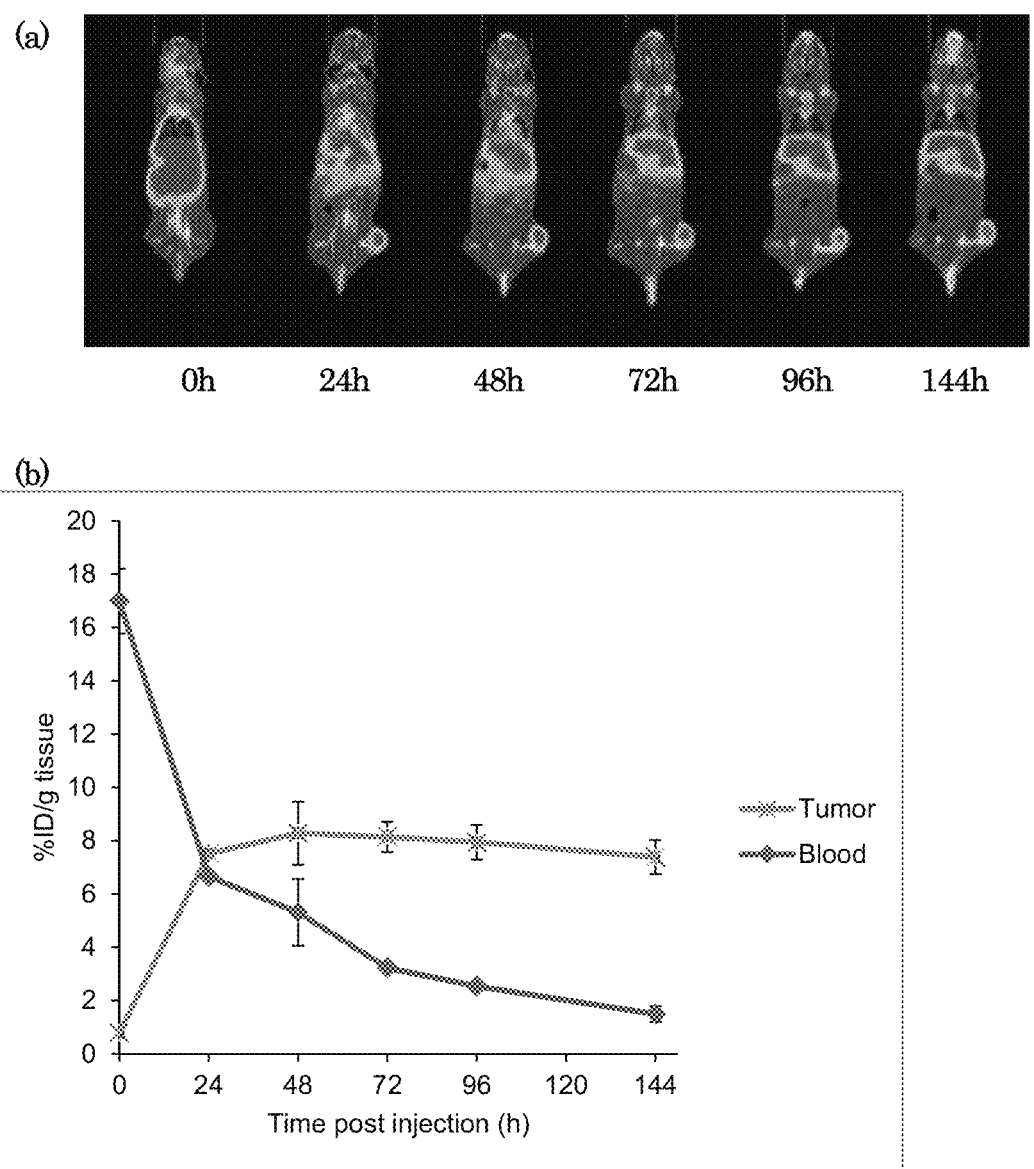
FIG. 10. (a) PET and CT images obtained using $^{89}$Zr-DFO-1125-IgG that recognizes human MSLM in model mice. (b) Graph showing changes over time in $^{89}$Zr radioactivity.

FIG. 10a shows PET and CT images after administration of $^{89}$Zr-labeled DFO-1125-IgG. Specific accumulation in the implanted tumor formed from NCI-N87, which is a cell line with high MSLN expression, was observed. FIG. 10b is a graph indicating changes over time in $^{89}$Zr radioactivity in the blood and NCI-N87 tumor obtained from the PET images. The data confirmed that while the labeled antibody was cleared from the blood over time after administration of the antibody, the antibody was taken up into the tumor expressing MSLN, and its accumulation was maintained.

(6) Small Animal PET Imaging (i) Method $^{89}$Zr-DFO-trastuzumab (7.2 MBq/100 μg) or $^{64}$Cu-labeled NOTA-trastuzumab was administered to mice with a tumor formed from SKOV3 cell line with high HER2 expression through their tail veins, and imaging was performed with a PET system (Clairvivo PET, Shimadzu, Kyoto, Japan) immediately after administration of $^{89}$Zr-DFO-trastuzumab and 24, 48, 72, and 120 hours after administration of $^{89}$Zr-DFO-trastuzumab, and immediately after administration of $^{64}$Cu-labeled NOTA-trastuzumab and 24 and 48 hours after administration of $^{64}$Cu-labeled NOTA-trastuzumab. Images were reconstructed from the collected data using 3D-DRAMA.

(ii) Results

FIG. 11 shows PET images after administration of $^{89}$Zr-labeled DFO-trastuzumab and $^{64}$Cu-labeled NOTA-trastuzumab. In both, high accumulation in the implanted tumor formed from SKOV3, which is a cell line with high HER2 expression, was shown from 24 hours after administration, and its accumulation increased over time. Notable $^{64}$Cu accumulation in the liver portion was also observed, but $^{89}$Zr accumulation in the liver was not observed.

The invention claimed is:

1. A polypeptide comprising any of the amino acid sequences of
   positions 1 to 272 of SEQ ID NO: 2,
   positions 1 to 269 of SEQ ID NO: 4,
   positions 1 to 270 of SEQ ID NO: 6,
   positions 1 to 268 of SEQ ID NO: 8,
   positions 1 to 273 of SEQ ID NO: 10, and
   positions 1 to 271 of SEQ ID NO: 12;
   said polypeptide having a specific affinity for mesothelin.

2. A tumor imaging agent comprising the polypeptide according to claim 1 conjugated to a labeling substance.

3. The tumor imaging agent according to claim 2, wherein said labeling substance is $^{89}$Zr.

4. A complex comprising the polypeptide according to claim 1 conjugated to an antitumor substance.

* * * * *